United States Patent
O'Halloran et al.

(10) Patent No.: US 10,792,640 B2
(45) Date of Patent: Oct. 6, 2020

(54) SORBENT MATERIAL FOR SEPARATING BIO-MACROMOLECULES

(71) Applicant: QuantuMDx Group Limited, Newcastle upon Tyne (GB)

(72) Inventors: Jonathan James O'Halloran, Newcastle upon Tyne (GB); Joseph H. Hedley, Newcastle upon Tyne (GB); Sam Whitehouse, Newcastle upon Tyne (GB); Marc Flanagan, Newcastle upon Tyne (GB); John Tyson, Newcastle upon Tyne (GB); Rachael Dixon, Newcastle upon Tyne (GB); Sam Bhatt, Newcastle upon Tyne (GB); Emily Crozier, Newcastle upon Tyne (GB); Chris Howell, Newcastle upon Tyne (GB)

(73) Assignee: QUANTUMDX GROUP LIMITED, Newcastle Upon Tyne (GB)

( * ) Notice: Subject to any disclaimer, the term of this patent is extended or adjusted under 35 U.S.C. 154(b) by 547 days.

(21) Appl. No.: 15/510,229

(22) PCT Filed: Sep. 10, 2015

(86) PCT No.: PCT/US2015/049519
§ 371 (c)(1),
(2) Date: Mar. 9, 2017

(87) PCT Pub. No.: WO2016/040697
PCT Pub. Date: Mar. 17, 2016

(65) Prior Publication Data
US 2017/0282154 A1    Oct. 5, 2017

Related U.S. Application Data

(60) Provisional application No. 62/048,754, filed on Sep. 10, 2014, provisional application No. 62/099,872, (Continued)

(51) Int. Cl.
*B01J 20/26* (2006.01)
*B01J 20/28* (2006.01)
(Continued)

(52) U.S. Cl.
CPC .......... *B01J 20/261* (2013.01); *B01J 20/103* (2013.01); *B01J 20/28004* (2013.01); (Continued)

(58) Field of Classification Search
None
See application file for complete search history.

(56) References Cited

U.S. PATENT DOCUMENTS 3,987,058 A * 10/1976 Saunders ........... B01J 20/28061
548/532
5,047,438 A * 9/1991 Feibush ................. B01J 20/26
521/122

(Continued)

FOREIGN PATENT DOCUMENTS

EP    0899567 A1    3/1999
GB    467900 A      6/1937
(Continued)

OTHER PUBLICATIONS

International Search Report dated Jan. 27, 2016 in International Application No. PCT/US2015/049519, filed Sep. 10, 2015.
(Continued)

*Primary Examiner* — Jill A Warden
*Assistant Examiner* — Brittany I Fisher
(74) *Attorney, Agent, or Firm* — Knobbe, Martens, Olson & Bear, LLP

(57) ABSTRACT

A sorbent material is disclosed for the one-step separation of bio-macromolecules in a single pass extraction of DNA from complex mixtures of molecules and chemicals. In one embodiment, the sorbent material comprises a silanized material at least partially coated or formed with a polymer selected from the group consisting of a poly(aryl methacrylate), a poly(aryl acrylate), a poly(heteroaryl methacrylate, a poly(heteroaryl acrylate) and a copolymer thereof.

14 Claims, 28 Drawing Sheets

Related U.S. Application Data filed on Jan. 5, 2015, provisional application No. 62/157,326, filed on May 5, 2015.

(51) Int. Cl.
  *C12N 15/10* (2006.01)
  *G01N 1/40* (2006.01)
  *B01J 20/32* (2006.01)
  *B01J 20/10* (2006.01)
  *B01J 20/286* (2006.01)

(52) U.S. Cl.
  CPC ......... *B01J 20/286* (2013.01); *B01J 20/2808* (2013.01); *B01J 20/28016* (2013.01); *B01J 20/28023* (2013.01); *B01J 20/28026* (2013.01); *B01J 20/28033* (2013.01); *B01J 20/28042* (2013.01); *B01J 20/28059* (2013.01); *B01J 20/28061* (2013.01); *B01J 20/28083* (2013.01); *B01J 20/28085* (2013.01); *B01J 20/3204* (2013.01); *B01J 20/327* (2013.01); *B01J 20/3276* (2013.01); *C12N 15/1006* (2013.01); *G01N 1/405* (2013.01); *B01J 2220/54* (2013.01)

(56) References Cited

U.S. PATENT DOCUMENTS

| | | | | |
|---|---|---|---|---|
| 5,470,463 | A * | 11/1995 | Girot | B01D 15/20 210/198.2 |
| 5,494,949 | A * | 2/1996 | Kinkel | B82Y 30/00 428/405 |
| 5,906,747 | A * | 5/1999 | Coffman | B01D 15/08 210/198.2 |
| 6,623,733 | B1 | 9/2003 | Hossainy et al. | |
| 6,787,307 | B1 * | 9/2004 | Bitner | C12N 1/02 435/5 |
| 9,187,647 | B2 * | 11/2015 | Greenwood | B82Y 30/00 |
| 2002/0088753 | A1 | 7/2002 | Huber | |
| 2003/0040621 | A1 * | 2/2003 | Tittgen | C12N 15/101 536/25.4 |
| 2004/0127648 | A1 | 7/2004 | Guerrier | |
| 2006/0057738 | A1 | 3/2006 | Hall, Jr. et al. | |
| 2006/0258798 | A1 | 11/2006 | Richard et al. | |
| 2007/0015191 | A1 * | 1/2007 | Bitner | C12N 15/1006 435/6.15 |
| 2008/0028986 | A1 * | 2/2008 | Futterer | C08G 65/3355 106/287.23 |
| 2008/0116137 | A1 | 5/2008 | Bonn | |
| 2008/0145272 | A1 | 6/2008 | Feaster et al. | |
| 2008/0154029 | A1 | 6/2008 | Balayan et al. | |
| 2010/0267109 | A1 | 10/2010 | Rothberg | |
| 2010/0279118 | A1 * | 11/2010 | Hempenius | B82Y 30/00 428/402.22 |
| 2011/0111987 | A1 | 5/2011 | Siegrist et al. | |
| 2011/0319506 | A1 | 12/2011 | Erbacher et al. | |
| 2013/0264287 | A1 * | 10/2013 | Zhang | C02F 1/40 210/639 |
| 2014/0039093 | A1 * | 2/2014 | Greenwood | C09D 5/028 523/212 |
| 2014/0179909 | A1 * | 6/2014 | O'Halloran | B01L 3/502707 536/25.41 |

FOREIGN PATENT DOCUMENTS

| | | |
|---|---|---|
| WO | WO 2000/006495 | 2/2000 |
| WO | WO 2014/079580 A1 | 5/2014 |

OTHER PUBLICATIONS

International Preliminary Report on Patentability dated Jan. 27, 2016 in International Application No. PCT/US2015/049519, filed Sep. 10, 2015.
Extended European Search Report, dated Jul. 2, 2018, in European Patent Application No. 15840160.4.
Iupac: aryl groups : Gold Book; In: IUPAC Compendium of Chemical Terminology, IUPAC, Research Triangle Park, NC, Jun. 12, 2009.
Singaporean Search Report, dated Mar. 6, 2018, in Singaporean Patent Application No. 11201701783Q.
Examination Report, dated May 31, 2019, in Singaporean Patent Application No. 11201701783Q.
Notice of Eligibility for Grant, dated Jul. 9, 2019, in Singaporean Patent Application No. 11201701783Q.
International Preliminary Report of Patentability, dated Sep. 26, 2016, in PCT Application No. PCT/US2015/049519.
Office Action, dated Mar. 26, 2020, in CN Application No. 2015800480707.

* cited by examiner

FIGURE 3
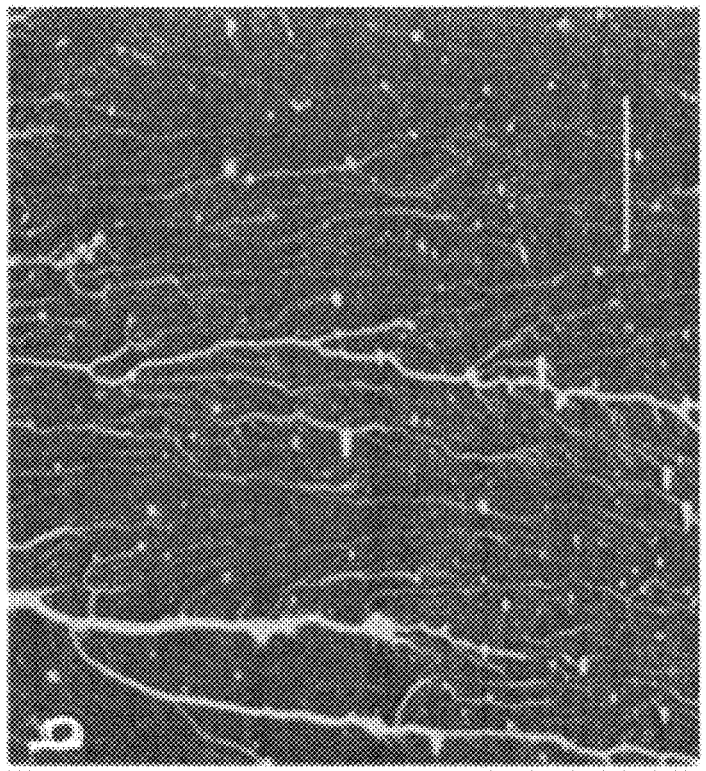
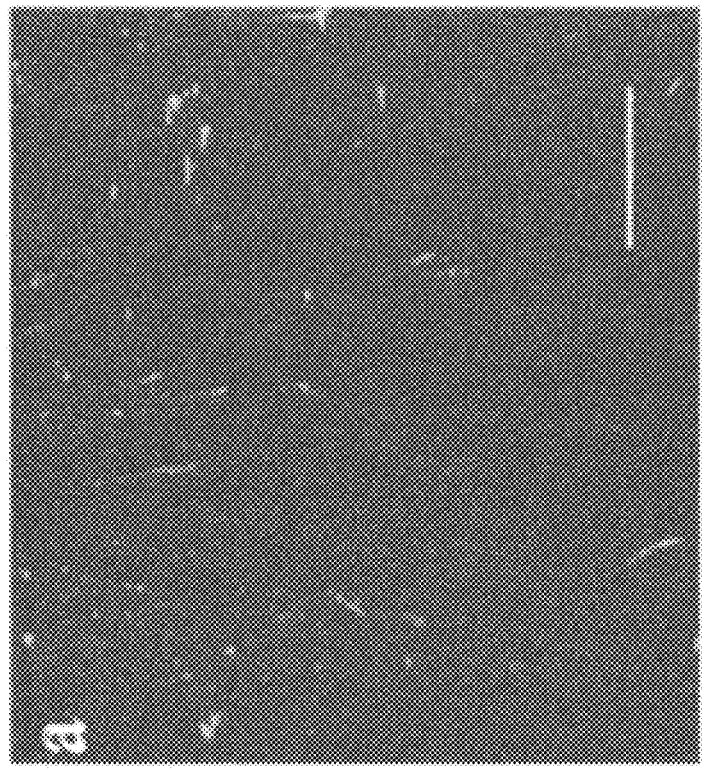

FIGURE 22 (continued)

B. Tissue

|  |  | -ve | 1 | 2 | 3 | 4 | 5 | Ave. | StD | Ave yield, µg |
|---|---|---|---|---|---|---|---|---|---|---|
| Alternative Spin Columns | DNA (µg/ml) | 3.3 | 22 | 24.1 | 24.6 | 25.7 | 13.1 | 21.9 | 5.1 | 4.4 |
|  | Protein (µg/ml) | 19.7 | 20 | 22.1 | 19.8 | 21.1 | 32.2 |  |  |  |
| QMDx Spin Columns | DNA (µg/ml) | 2.7 | 22.4 | 27.3 | 26.8 | 25.8 | 29.9 | 26.4 | 2.7 | 4 |
|  | Protein (µg/ml) | 10.2 | 11.3 | 12 | 10.4 | 10 | 14.1 |  |  |  |

C. Bacterial Plasmids

|  |  | -ve | 1 | 2 | 3 | 4 | 5 | Ave | StD | Ave yield, µg |
|---|---|---|---|---|---|---|---|---|---|---|
| Alternative Spin Columns | DNA (µg/ml) | 0 | 0.45 | 0.14 | 0.24 | 0.28 | 0.27 | 0.28 | 0.11 | 13.8 |
|  | Protein (µg/ml) | <10 | <10 | <10 | <10 | <10 | <10 |  |  |  |
| QMDx Spin Columns | DNA (µg/ml) | 0 | 2.22 | 1.94 | 2.17 | 2.04 | 2.19 | 2.11 | 0.12 | 844.8 |
|  | Protein (µg/ml) | <10 | <10 | <10 | <10 | <10 | <10 |  |  |  |

D. Buccal Swabs

|  |  | -ve | 1 | 2 | 3 | 4 | 5 | Ave | StD | Ave yield, µg |
|---|---|---|---|---|---|---|---|---|---|---|
| Alternative Spin Columns | DNA (µg/ml) | <0.1 | 3 | 2.6 | 2 | 4 | 3.1 | 2.9 | 0.7 | 441.9 |
|  | Protein (µg/ml) | <10 | <10 | <10 | <10 | <10 | <10 |  |  |  |
| QMDx Spin Columns | DNA (µg/ml) | <0.1 | 2.4 | 2.4 | 2.5 | 2.4 | 2.1 | 2.4 | 0.1 | 711.6 |
|  | Protein (µg/ml) | 17.2 | 22.5 | 25.1 | 24.3 | 25.4 | 19.7 |  |  |  | ized inorganic material at least
SORBENT MATERIAL FOR SEPARATING BIO-MACROMOLECULES

INCORPORATION BY REFERENCE TO ANY PRIORITY APPLICATIONS

The present application is a national phase of PCT Application No. PCT/US2015/049519, filed Sep. 10, 2015, which claims priority from U.S. Provisional Application No. 62/048,754, filed Sep. 10, 2014, U.S. Provisional Application No. 62/099,872, filed Jan. 5, 2015, and U.S. Provisional Application No. 62/157,326, filed May 5, 2015, the contents of each of which are incorporated by reference in its entirety. Any and all applications for which a foreign or domestic priority claim are identified in the Application Data Sheet filed with the present application are hereby incorporated by reference under 37 CFR 1.57.

BACKGROUND

DNA is an anionic polymer consisting of subunits called nucleotides, which together form molecules called nucleic acids. DNA was first identified and isolated by Friedrich Miescher in 1871. The double helix structure of DNA was deduced by James Watson and Francis Crick 1953.

Natural nucleobases can be one of four subunits adenine (A), cytosine (C), guanine (G) & thymine (T). Double stranded DNA (dsDNA) comprises two long chains of nucleotides comprising the different nucleotide bases (e.g. AGTCATCGTAGCT) with a backbone of alternating phosphate and sugar residues joined by phosphodiester bonds. The nucleobases are classified into two types: the purines, A and G, being fused five- and six-membered heterocyclic compounds and the pyrimidines, the six-membered rings C and T.

In a DNA double helix, each type of nucleobase on one strand hydrogen bonds with just one type of nucleobase on the other strand. This is called complementary base pairing. Here, purines form hydrogen bonds to pyrimidines, with adenine preferentially bonding only to thymine via two hydrogen bonds and cytosine bonding to guanine by three hydrogen bonds. This double stranded antiparallel structure (dsDNA) is maintained largely by the intra-strand base stacking interactions, which are strongest for G, C sequences. The stability of the dsDNA form depends not only on the GC-content (% G, C base pairs) but also on sequence (since stacking is sequence specific) and also length (longer molecules are more stable). The stability can be measured in various ways; a common way is the 'melting temperature', which is the temperature at which 50% of the double stranded molecules are converted to single stranded molecules. Melting temperature is dependent on ionic strength and the concentration of DNA. As a result, it is both the percentage of GC base pairs and the overall length of a DNA double helix that determines the strength of the association between the two strands of DNA. Long DNA helices with a high GC-content have stronger interacting strands, while short helices with high AT content have weaker interacting strands. This reversible and specific interaction between complementary base pairs is critical for all the functions of DNA in living organisms.

The two strands of a DNA double helix run in opposite directions to each other (anti-parallel), one backbone being 3' (three prime) and the other 5' (five prime) with the 5' end having a terminal phosphate group and the 3' end a terminal hydroxyl group. It is the sequence of these four nucleobases along the backbone that encodes genetic information, which specifies the sequence of the amino acids within proteins.

The structure of DNA of all species comprises two helical chains each coiled round the same axis, each with a pitch of 34 angstroms (3.4 nanometers) and a radius of 22 angstroms (2.2 nanometers).

As the strands are not symmetrically located with respect to each other, two grooves of unequal size can be found in the structure. One groove, the major groove, is 22 Å wide and the other, the minor groove, is 12 Å wide. The narrowness of the minor groove means that the edges of the bases are more accessible in the major groove. As a result, proteins like transcription factors that can bind to specific sequences in double-stranded DNA usually make contacts to the sides of the bases exposed in the major groove.

Sorbent materials for one-step separation of DNA from other bio-macromolecules as well as low molecular weight compounds have been sought to aid in rapid and/or automated DNA analysis from biological samples, including solutions, suspensions, tissue extracts and fixed samples. For some applications, it is further desirable that the material allows preferential retention of either the DNA or the non-DNA impurities—thereby potentially facilitating purification of the DNA.

SUMMARY

Embodiments of the present disclosure are related to a sorbent material for the one-step separation of bio-macromolecules in a single flow through channel. The sorbent material includes a silanized inorganic material at least partially coated with a polymer selected from the group consisting of a poly(aryl methacrylate), a poly(aryl acrylate), a poly(heteroaryl methacrylate), a poly(heteroaryl acrylate) and a copolymer thereof. The use of a combination of particle size, hydrophobic and hydrophilic monomer units to create distinct structures on the surface of the materials are described herein. New co-monomer units provide a one-pot solution to tailoring the surface properties before polymerization and surface immobilization. Throughout this disclosure blood is used as an example sample type only; other sample types such include, but are not limited to; tissue, swabs, sputum and urine may be used. The sample types described herein are in no way limiting the range of use of the present disclosure.

Materials and methodologies that provide at least some of the desired performance features, include but are not limited to bulk porous polymers, gels, electrospun mats/plugs, co-extrusion of polymers, sacrificial salts or dissolvable polymers to create pores, porous silicon nanostructures (solid constructs) and hard templates/membrane production.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be unsubstituted or substituted, e.g., substituted with methyl or methoxy, and the connection of the aryl group to other parts of a larger molecule may be via the aryl ring or via the substituent. Examples of aryl groups that are substituted include benzyl, hydroxybenzyl, 2-phenylethyl, benzhydryl, triphenylmethyl, anisolemethyl, phenylethanol, and naphthalenemethyl.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted. e.g., substituted with methyl or methoxy, and the connection of the heteroaryl group to other parts of a larger molecule may be via the heteroaryl ring or the substituent. Pyridinemethyl and thiophen-3-ylmethyl are examples of heteroaryl groups that are substituted.

In one aspect, the disclosures provided herewith relate to a sorbent material for separating bio-macromolecules. The sorbent material may comprise a silanized material at least partially coated or formed with a polymer selected from the group consisting of a poly(aryl methacrylate), a poly(aryl acrylate), a poly(heteroaryl methacrylate, a poly(heteroaryl acrylate) and a copolymer thereof.

In one variation, the silanized inorganic material is selected from the group consisting of a silanized silica particle, a silanized silica fiber and a silanized silica membrane.

In one variation, the silanized material is an organic material selected from the group consisting of porous organic materials and membranes.

In another variation, the polymer includes a recurring unit selected from the group consisting of anisolemethyl methacrylate, phenylethanol methacrylate, pyridinemethyl methacrylate and naphthalenemethyl methacrylate.

In another variation, the sorbent material has a wettability value in the range of about 65° to about 100°.

In another variation, the sorbent material has a surface area in the range of about 0.1 m² to about 130 m².

In another variation, the silanized inorganic material includes silanized silica particles having an average pore size in the range of about 1 nm to about 100 nm.

In one embodiment, the average pore size is about 30 nm.

In another variation, the silanized inorganic material includes silanized silica particles having an average diameter of less than about 200 microns.

In one embodiment, the average diameter is about 15 microns.

In another embodiment, an article is disclosed. The article includes the above-described sorbent material including a silanized inorganic material at least partially coated with a polymer selected from the group consisting of a poly(aryl methacrylate), a poly(aryl acrylate), a poly(heteroaryl methacrylate, a poly(heteroaryl acrylate) and a copolymer thereof.

The article may be in a form selected from particulate, monolithic or membrane-like. The average interstitial distance may be greater than about 10 nm.

In a variation, the average interstitial distance is less than about 12 microns.

In another variation, the article is in the form of a membrane, and the sorbent material is embedded in a porous organic or inorganic matrix.

A method is disclosed for making a sorbent material comprising silanized silica at least partially coated with poly(benzyl methacrylate). The method includes: suspending silica in a solution of dimethylvinylchlorosilane in trifluorotoluene; removing the liquid and resuspending the silica in a fresh solution of dimethylvinylchlorosilane in trifluorotoluene; optionally removing the liquid and resuspending the silica again in a fresh 5% solution of dimethylvinylchlorosilane in trifluorotoluene; collecting and drying the resulting silanized silica; adding the silanized silica, benzylmethacrylate and potassium peroxodisulfateto a stirred solution of sodium stearate in water; and collecting and drying the resultant sorbent material comprising silanized silica coated with poly(benzyl methacrylate).

In still another aspect, the disclosures provided herewith relate to a dual processing device for lysing a biological sample and isolating nucleic acids from the biological sample. The device comprises a sample input unit, a sample lysis unit, a nucleic acid extraction unit, and a nucleic acid reception unit. The nucleic acid extraction unit comprises a silanized material at least partially coated or formed with a polymer selected from the group consisting of a poly(aryl methacrylate), a poly(aryl acrylate), a poly(heteroaryl methacrylate, a poly(heteroaryl acrylate) and a copolymer thereof. The silanzied material is configured to retain proteins and other non-nucleic acids from the biological sample and allow the nucleic acids to pass through into the nucleic acid reception unit.

In one variation, the sample lysis unit comprises a blade that is configured to rotate within the sample lysis unit so as to lyse the biological sample.

In one variation, the sample lysis unit comprises beads.

In one variation, the device further comprises a spring loaded plunger that is configured to control rotation of the blade in the sample lysis unit.

In one variation, the device further comprises a buffer that is configured to act as a mobility carrier when the biological sample is processed in the sample lysis unit and/or the nucleic acid extraction unit.

In one variation, the nucleic acid reception unit comprises a cap.

In one variation, the cap is a pressure sealed cap that can be removed from the device.

In still another aspect, the disclosures provided herewith relate to a sorbent material for separating bio-macromolecules. The sorbent material comprises a silanized material at least partially coated or formed with a polymer, wherein the sorbent material comprises an average interstitial spacing of greater than about 6 um and less than about 23 um, a pore size of greater than about 10 nm and less than about 200 nm, and a surface area of greater than about 0.1 m² and not more than about 150 m².

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIG. 3 shows typical AFM images obtained from this study. Contact angles greater than 70° were shown to prevent DNA adhesion (FIG. 3a), while values below 60° result in wholesale deposition of material (FIG. 3b).

DETAILED DESCRIPTION

Figure 1:
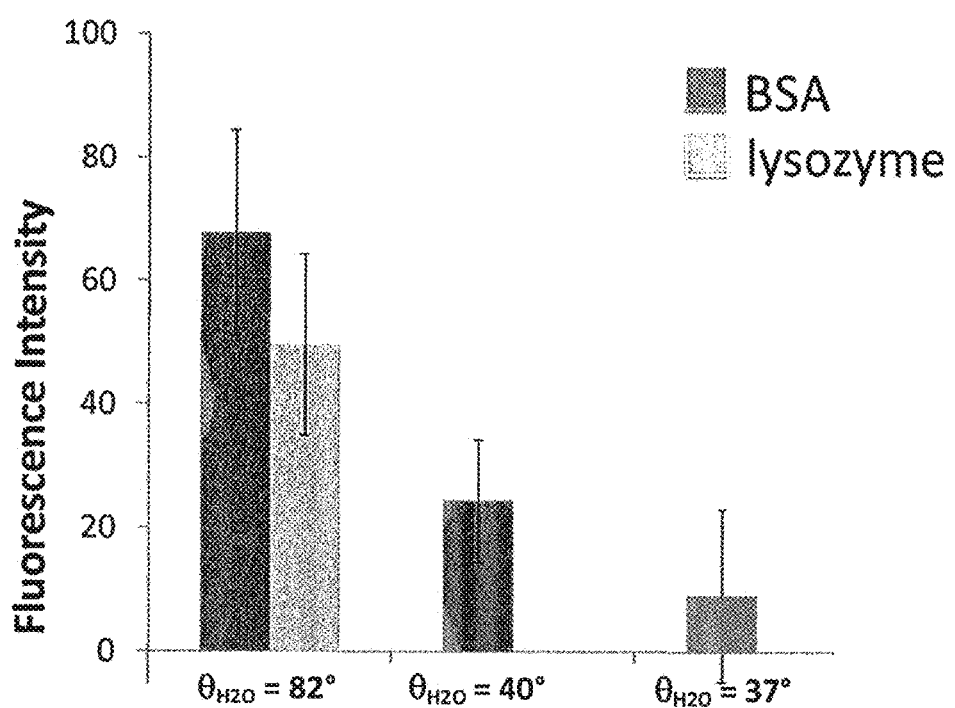
FIG. 1 shows protein adsorption as a function of contact angle determined by fluorescence intensity.

Free DNA in blood lysate is not readily accessible for sensitive molecular analysis. Lysed blood is a highly complex mixture of lipids, proteins, salts and other cellular and non-cellular material. Much of this material is inhibitory to downstream analysis of nucleic acids (DNA/RNA). Purification of nucleic acid from this complex lysate mixture permits analysis by molecular and non-molecular techniques. For example, the biochemistry of the polymerase chain reaction is inhibited by hemoglobin present in blood lysate. Purification of DNA from the blood lysate removes hemoglobin and allows PCR to be performed with significantly greater efficiency. For some applications, it is further desirable that the material allows preferential retention of either the DNA or non-DNA impurities-thereby facilitating purification of the DNA.

To study or analyze the sequence and biology of DNA from a sample it is usually necessary to extract or isolate the nucleic acid from the rest of the clinical or biological sample (i.e. other cellular components such as lipids, carbohydrates, proteins etc.) The standard methodology for achieving isolation of DNA in this manner consists of a protocol with different variations depending upon application and sample type, begins with cell disruption or cell lysis, to release the DNA. This is commonly achieved by mechanical lysis (such as grinding or grinding tissue in liquid nitrogen), sonication, enzymatically or chemically (such as adding a chaotropic salts (e.g. guanidiniumthiocyanate) to the sample). The cells lipid membranes and other lipids, are usually removed by adding a detergent and the proteins unusually removed by adding a protease (such as Protinase K, optional but almost always done). Water-saturated phenol, chloroform allows for phase separation by centrifugation of a mix of the aqueous sample and a solution, containing resulting in an upper aqueous phase, while proteins are found in the organic phase. In a last step, RNA is recovered from the aqueous phase by precipitation with ice cold 2-propanol or ethanol. DNA will be located in the aqueous phase the absence of guanidiumthiocynate. Since DNA is insoluble in these alcohols, it will precipitate and aggregate, giving a pellet upon centrifugation. This step also removes alcohol-soluble salt. Adding a chelating agent to sequester divalent cations such as $Mg^{2+}$ and $Ca^{2+}$ prevents DNAse enzymes from degrading the DNA. Cellular and histone proteins bound to the DNA can be removed either by adding a protease or by having precipitated the proteins with sodium or ammonium acetate, or extracted then with phenol-chloroform mixture prior to the DNA-precipitation.

In another method, DNA is isolated from a lysate (regardless of what method of lysis is used) by virtue of its ability to bind to in the presence of high concentrations of chaotropic salts. The DNA can bind to any silica surface, whether this is pillars with a microfluidic cassettes, silica coated paramagnetic beads, a silica filter within a spin column or other silica surface. The chaotropic salts are then removed with an alcohol-based wash and the DNA eluted in a low ionic strength solution such as TE buffer (a buffer consisting of trishydroxymethylaminomethane ('Tris') and ethylenediaminetetraacetic acid ('EDTA')) or water. DNA binds to silica because of dehydration and hydrogen bond formation, which competes against weak electrostatic repulsion. Hence, a high concentration of salt will help drive DNA adsorption onto silica and a low concentration will release the DNA. As the DNA is bound to the silica surface the rest of the cellular and other debris is simply washed away with wash buffers prior to eluting the DNA bound to the silica in either $H_2O$ or TE buffer.

The CHARGESWITCH® (Invitrogen) methodology sees negatively charged DNA (through their negatively charged phosphate backbone) in lysate bind to a special ligand that acquires a positive charge at low pH (<6.5). Proteins and other impurities removed from the CHARGESWITCH®-bound nucleic acids through the use of aqueous wash buffers. Nucleic acids can then be released from the CHARGESWITCH® ligand when the pH of the surrounding media is raised (>8.5) and the positive charge is neutralized.

The Nexttec DNA isolation system, allows purifying DNA with a single centrifugation step within four minutes following cell lysis. It is up to five times faster than other currently used DNA isolation systems. This is possible through proprietary sorbent matrix, which in a reversal of silica based methods, retains inhibiting substances, such as proteins and low molecular weight substances, and allows the pure DNA within a lysed sample to pass through. One limitation of this method is that it relies on a long enzymatic lysis step at 60° C.

Separation of complex mixtures is typically performed using chromatographic methods. Here, a liquid and a sample mixture are passed through a column filled with a sorbent, leading to the separation of the sample components. The active component of the column, the sorbent, is typically a granular material made of solid particles (e.g. silica, polymers), 2-50 micrometers in size. The components of the sample mixture are separated from each other due to their different degrees of interaction with the sorbent particles. The liquid is typically a mixture of solvents (e.g. water, buffer, acetonitrile and/or methanol) and is referred to as a 'mobile phase'. Its composition and temperature play a major role in the separation process by influencing the interactions taking place between sample components and sorbent. These interactions are physical in nature, such as hydrophobic (dispersive), dipole-dipole and ionic, most often a combination.

Silica particles used in column chromatography are typically formed from tetraethoxysilanes which are partially hydrolyzed to polyethoxysiloxanes to form a viscous liquid which emulsifies in an ethanol water mixture through vigorous stirring. This stirring causes the particles formed to be spherical and these spheres are converted to silica hydrogels through catalytically induced hydrolytic condensation (the 'Unger' method), which causes extensive crosslinking via the surface silanol species. The hydrogel spheres are then heated (dried) to produce a xerogel. The pH, temperature, catalysts and solvents as well as the silica sol concentration all act to control the particle and pore size of the highly porous silica xerogel (sometimes called sol-gel) materials.

An alternative process uses silica microparticles which are then aggregated in solution using a urea/formaldehyde reagent to produce particles consisting of agglomerated microspheres—the so called 'sil-gel' materials. The concentration and diameter of the microparticles as well as the reaction conditions, control the particle size and pore size of the resulting sil-gel particle.

The particle size of the silica spheres controls the efficiency of the silica material and refers to the average diameter of the silica particles. Backpressure is inversely proportional to the particle size and chromatographic efficiency is inversely proportional to particle size Small particles (<2 μm) are typically used for high-resolution separations using longer columns, or high-speed separations using shorter columns. While 5-10 μm particles are used for routine analyses of less complex samples or for preparative chromatography where analyte capacity (loading) is of high importance.

Silica particles for chromatography have very high surface area, a property that is required for good analyte retention. Most of the surface area is contain in the internal pore structure of the silica particles which have over 99% of the available surface area. A typical surface area for the silica used for chromatography is around 330 $m^2$/g and in a 150×4.6 mm column there may be as much as 1.5 g of silica.

The surface area of the particle is inversely proportional to the pore diameter and therefore a 3 mm particle with a 120 nm pore diameter will have more than twice the surface area of a 3 μm particle with a 300 nm pore diameter. Pore diameters in the range 8-12 nm are typically used for the analysis of small molecules (<3,000 Da), which can easily penetrate into the pores and access a great majority of the silica surface. These small pore columns are not useful for the analysis of larger molecules such as peptides or proteins, which are excluded from the pore due to their larger hydrodynamic volume. Typically the pore diameter needs to be three times the times the hydrodynamic diameter of the analyte in order to be accessible.

Theoretically, the van Deemter equation (Eqn1) can be used to describe the variance per unit length of a separation column to the linear mobile phase velocity with respect to physical, kinetic and thermodynamic properties of separation. Here, the resolving power of the column is described in terms of flow and kinetics.

$$H = 2\lambda d_p + \frac{2\gamma D_m}{u} + \frac{\omega (d_p \text{ or } d_c)^2 u}{D_m} + \frac{R d_f^2 u}{D_s} \qquad \text{Eqn 1}$$

Where, H is plate height, λ is particle shape (with regard to the packing), dp is particle diameter, γ, ω, and R are constants, Dm is the diffusion coefficient of the mobile phase, dc is the capillary diameter, df is the film thickness, Ds is the diffusion coefficient of the stationary phase and u is the linear velocity. Evidently, reducing the particle size of the packing material enhances the column efficiency and optimal mobile phase linear velocity, allowing faster analysis. However, though micro particle packing materials provide such advantages, they also have the disadvantage of increasing pressure losses in the column. Therefore, packing material particle size must be optimized to take advantage of the benefits of increased speed and higher separation, while mitigating its disadvantage of pressure.

The particle size distribution is another key parameter that should be considered. Particle size is stated as a mean value from a distribution of particle sizes, achieved practically by the manufacturer using automated sub-sieve sizing techniques. In reality a wide distribution of particles will lead to heterogeneity within the column and, as such, an increase in variable path lengths the analyte molecules can take through the column.

It is well know that proteins may be absorbed physically to the vast majority of organic and inorganic surfaces. In this regard, the opportunity to tune the structure of organic polymers presents a great deal of potential for tailoring surface properties. In such applications, the polymer acts as a discriminatory matrix for biological immobilization or repulsion. The ability to synthetically modify monomer units to introduce further functionality; functionality that may be exploited post polymerization presents to opportunity to tailor the physical and chemical structure of functional groups presented at the surface to perform specific roles within the filtrate-substrate interface. Additionally, recent years have seen a growing emphasis placed upon the fabrication of materials with nanoscale dimensions. In particular, attention has focused on devising methods for producing highly anisotropic forms of polymer such as nanowires, nanofibers and nanotubes.

Nanostructures of polymers have attracted growing interest due to the potential advantages of combining these materials with low dimensionality. Materials with dimensions in the nanometer regime have a number of highly desirable characteristics such as readily tunable surface properties, high mechanical flexibility greater biocompatibility than many inorganic materials and high surface area. Nanofibrous membranes and nanofiber composites can be produced in a number of ways including drawing, hard/soft template synthesis, self-assembly and electro spinning.

Template-directed growth is the most frequently used approach for preparing such 1-D nanostructures and several different methods have been shown to be effective. Here, an external 'membrane' is used to direct the growth of the polymer into the desired architecture. A variety of alternative materials have been used to facilitate this process which can be broadly split into two categories; 'hard' or 'soft' templates.

The use of 'hard' templates was pioneered by Martin et. al. This method entails using nanoscopic pores as a host membrane and follows a rather simplistic 3-step approach, 1) fill the nanoscale pores of a membrane with a monomer, 2) polymerize the monomer inside the pores, and 3) remove the template in order to obtain the pure polymer. The diameter and morphology of the structures created are determined by the pores or channels of the template employed. In recent years, the most commonly used hard-templates have been an alumina film containing anodically etched pores (porous silicon is generated by anodically etching crystalline silicon in aqueous or non-aqueous media with pore size and thickness is determined by the current). These membranes can be prepared from aluminum metal with pores arranged in a regular hexagonal lattice of relatively high densities. A range of pore sizes have been synthesized and some as small as 5 nm have been reported.

Using this approach, the Martin group in particular have synthesized a number of nanostructures of polyaniline (PAni), polypyrrole (PPy), poly(pyrrolepropylic acid), polyaniline and polythiophene (PTh), using anodized aluminum oxide, porous silicon and track-etched polycarbonate membranes as templates. The only prerequisite for creating nanostructures of polymers in this fashion is to be able to load the pores with the precursor materials.

This can vary in difficulty depending on the monomer of interest and the membrane used. The different methods used to load the pores include negative pressure, liquid phase injection, vapour phase deposition or submerging the template into a solution of the monomer. The latter method allows good control over the length of the structure produced by controlling the amount of monomer passed through the pores. Polymerization of monomer-filled pores can be achieved by the addition of a chemical oxidizing agent or, more commonly, through electrochemical polymerization.

The soft-template method is another relatively simple, cheap and powerful approach for fabricating polymer nanostructures. This method is based on selective control of non-covalent interactions, such as hydrogen bonds, van der waals forces, $\pi$-$\pi$ stacking, co-ordination and dispersive forces to direct the self-assembly of nanoscale polymeric materials. To date, colloidal particles, oligomers, soap bubbles and colloids have all been implemented as soft templates to prepare wire, ribbons and sphere like nanostructures. For example, PPy nanotubes (~94 nm in diameter and ~2 mm in length) have been synthesized using sodium bis(2-ethylhexyl) sulfosuccinate (AOT) reverse cylindrical micelles as a soft-templates.

Pre-existing 1-D nanostructures such as naturally occurring biopolymers can also serve as useful soft-templates or seeds in order to direct the growth of polymer nanowires. Polymer nanostructures produced in this manner are often composite core-sheath materials consisting of a biopolymer core and a polymer sheath, eliminating the need to remove the template post-synthesis. In contrast to templating in porous media, this approach yields hybrid supramolecular polymers, a relatively recent class of material. Largely owing to their ability to self-assemble and form highly complex supramolecular structures, biological molecules provide an impressive arsenal for use in the construction of supramolecular nanoscale structures with a number of strategies explored.

Electro spinning represents an alternative method by which polymer nanofibers may be formed. Here, the application of a high voltage to induce the formation of a liquid jet of polymer solution or melt. The basic electro spinning setup has 3 major components: a high-voltage power supply, a capillary device and a ground collector. As a pump forces the polymer out the capillary, a high-voltage electric charge is applied which charges the pendant drop of the polymer liquid at the nozzle. The application of a high electric field to the polymer flowing from the capillary tube induces surface electrical charges, which as soon as the surface tension is overcome, causes ejection of a thin polymer jet, which moves towards the collector. The electrified jet undergoes stretching and whipping resulting in a long thin fiber. As the electrified jet is continuously extended and the solvent evaporates, there is a significant reduction in the diameter of the jet from several hundred micrometers to tens of nanometers. The charged fiber is deposited onto the collector plate such as a nonwoven mat of fibers.

The electro spinning process is affected by a number of different factors and thus control of these factors enables the formation of nanofibers with desired dimensions. By tailoring the electro spinning process fibers that are flat, cylindrical, have beads inserted or pores can be made. Operating conditions and polymer solution properties define many of the properties of the nanofiber produced. By altering the collector you can choose whether you get random or aligned fibers. For example, you could use a rotating cylinder, a rotating wire drum, or a disc collector.

The use of polymeric materials to form or impart desired functionality and properties over a given surface area, for the separation of DNA from other cellular material in a single pass technology, including but not limited to being packed into a microfluidic channel, a pipette tip, a vacuum plate, a spin column etc., is described herein. Specifically, we have used a combination of a well-defined active surface area, hydrophobic and hydrophilic properties, and specific monomer unit characteristics to create distinct surface terminations in the formation or modification of suitably sized constructs to provide separation of complex biological mixtures such as blood lysate.

At least some of the desired performance features, include but are not limited to: bulk porous polymers, gels, electrospun mats, co-extruded polymers, sacrificial salts, dissolvable polymers to enable pore creation, porous silicon nanostructures and hard/soft templates modified with appropriate monomer or polymer units.

Monolithic polymers combine many advantageous features of these approaches and have seen considerable interest in recent chemical separation literature and particularly lend themselves to direct incorporation into fluidic devices. Monolithic columns create a "single large particle" featuring interconnecting pores that form a continuous skeleton. This macroporous structure gives monoliths multiple unique characteristics including high permeability and high mass transfer, allowing for high flow rates at low pressures.

In the following description, reference is made to the accompanying drawings, which form a part hereof. The illustrative embodiments described in the detailed description, drawings and claims are not meant to be limiting. Other embodiments may be utilized and other changes may be made, without departing from the spirit or scope of the subject matter presented herein. It will be readily understood that the aspects of the present disclosure, as generally described and illustrated herein, can be arranged, substituted, combined, separated and designed in a wide variety of different configurations, all of which are explicitly contemplated herein. All data and images disclosed in the detailed description and examples have been generated by the applicant.

Protein Adsorption

Physisorption of proteins is a complex process influenced by many factors related to electrostatic and hydrophobic interactions between substrate and molecule. Adsorption of proteins to modified surface sis shown to exhibit a general dependence on the wettability of the surface. Proteins preferentially adsorb to hydrophobic surfaces (high contact angle). Small proteins such as lysozyme (14.3 kDa, pI 11.4) show weak adsorption to hydrophobic surfaces. While larger proteins such as bovine serum albumin (66.5 kDa, pI 4.7), adsorbmore to hydrophilic surfaces (low contact angle).

To investigate protein adsorption as a function of contact angle, we spotted samples with fluorescently labeled protein (BSA-CF568 and lysozyme-CF568). After incubation in a humidity chamber followed by rinsing, samples were investigated under a confocal fluorescence microscope. FIG. 1 shows protein adsorption as a function of contact angle determined by fluorescence intensity. From the results shown, it can be concluded that higher contact angle values (>40) result in the adsorption of both large and small proteins to the surface.

DNA Repulsion

The adsorption of DNA onto surfaces presenting Si—O functionalities such as mica and silicon dioxide is well known. Treatment of such surfaces with an appropriate alkyl silane modifies the substrate to produce a hydrophobic surface termination. Such treatment is known to reduce surface interactions with DNA and thus promote discrimination against DNA adhesion.

Figure 2:
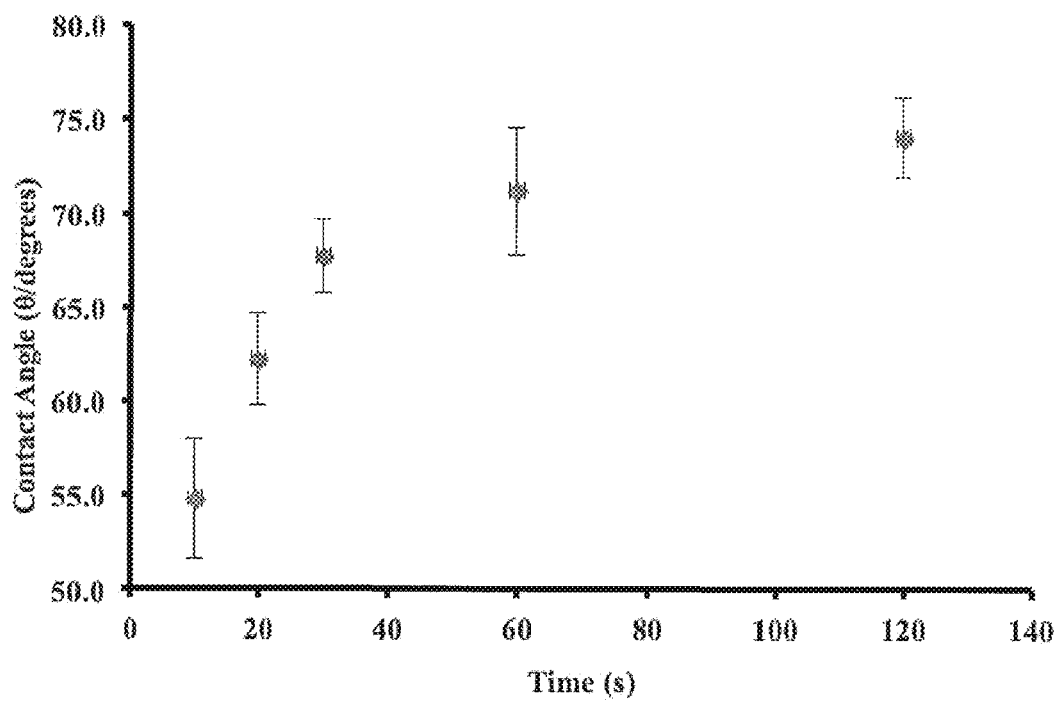
FIG. 2 shows the change in contact angle for a droplet of nanopure water deposited onto $Si/SiO_2$ substrates with varied exposure time to alkyl silane.

In order to gain further understanding surface wettability of silanized silicon dioxide, we focused upon determining the contact angle and therefore hydrophobicity of the silicon surface to various incubation times in relation to DNA adhesion. FIG. 2 shows the change in contact angle for a droplet of nanopure water deposited onto Si<111> substrates with varied exposure time to alkyl silane.

Clearly, the contact angle significantly increased initially and then plateaued after ~20 seconds exposure. The data shows that at these shorter exposure times (20-60 seconds), it is considered that only a fraction of the surface is modified. With longer exposure times (>60 seconds), it would seem the entire surface is modified.

Following silanization of $Si/SiO_2$ surfaces, an aliquot DNA solution was combed across the wafer using a pipette tip at a range of contact angles. FIG. 3 shows typical AFM images obtained from this study. Contact angles greater than 70° were shown to prevent DNA adhesion (FIG. 3a), while values below 60° result in wholesale deposition of material (FIG. 3b). $Si/SiO_2$ may refer to, at least in some embodiments, a crystal structure of a bulk silicon substrate used to mimic the surface properties of silica particles. More commonly referred to $Si/SiO_2$ in certain embodiments may be a layer of silicon covered by a layer of silicon dioxide—the substantially similar or same surface termination as silica.

Biological Activity as a Function of Wettability

To find the fine balance surface for large and small proteins adsorption whilst excluding DNA adsorption, we assessed a range of monomer units and combinations thereof for their performance properties as a function of surface wettability characteristics. Here, N-doped $Si/SiO_2$ wafers were cleaned and modified with each monomer system and contact angles taken over a range of samples. Table 1 summarizes the results of 16 different polymer systems studied.

Based on these findings we proceeded to examine the performance characteristics of each system as a function of wettability. For this study we used silica gel particles ~15 μm in diameter and with 300 Å pores. Briefly, DNA extraction cassettes (DECs)—designed to hold 100 mg sorbent—were filled with compounds or with unmodified silica, and used to purify DNA from 40 μl of blood lysate (generated by mechanical lysis using bead beating) or from Lysis Buffer alone. DNA extraction cassettes can be, but not limited to, molded or milled thermoplastic architectures with microdimensions capable of holding sorbent material and passing fluid such as lysed blood through the packed material. The form factor of DECs can be serpentine in nature, thick, thin and also a fully integrated cassette. The packing and function of the described sorbent material is independent of the vessel holding the material. Indeed, other vessels such as spin-columns have also been used to perform DNA-extraction from blood, cell free DNA from Serum and E. coli spiked in dirty water, among other sample matricies. Quantification of DNA and protein in fractions from DECs packed with a range of compounds. DNA was eluted into 300 μl fractions using a flow rate of 100 μl/min, and samples of these fractions were used for DNA and protein quantification using a Qubit 2.0 fluorometer (Invitrogen). DNA concentrations were also determined using real-time quantitative PCR (RT-qPCR): 5 µl of fractions were added to RT-qPCR reactions including 12.5 µl 2× Rotor-Gene SYBR Green PCR Master Mix (QIAGEN), 0.25 µl 100 µM CYP2C9*3f (forward primer), 0.25 µl 100 µM CYP2C9*3r (reverse primer) and deionized water to make up to final volumes of 25 µl. RT-qPCR was performed using a Rotor-Gene Q cycler (QIAGEN) using the following reaction conditions: 95°, 5 mins; 95° C., 10 secs; 58° C., 20 secs; 72° C., 20 secs; repeat last three steps (×44), 50-99° C. (melt). DNA concentrations were then determined by comparing cycle threshold (Ct) values to those of human gDNA standards of known concentration.

TABLE 1

Contact Angles for Alternative Polymer Systems

| Monomer Unit | Average contact Angle |
|---|---|
| 4-Vinylphenol, divinyl benzene and methacrylic acid | 85.5 |
| 4-chlorostyrene, allyl alcohol and divinylbenzene | 94.8 |
| Ethyl Methacrylate | 87.0 |
| Ethyl Methacrylate and Styrene | 81.9 |
| Ethyl Methacrylate, Divinylbenzene and Styrene | 93.6 |
| 2-Hydroxyethyl Methacrylate | 57.0 |
| 2-Hydroxyethyl Methacrylate and Styrene | 82.9 |
| Styrene | 95.3 |
| Divinylbenzene | 99.5 |
| Furfuryl Methacrylate | 82.8 |
| Cyclohexyl Methacrylate | 97.1 |
| Benzyl Methacrylate | 83.5 |
| Benzyl Methacrylate and Styrene | 90.7 |
| Benzyl Methacrylate, Divinylbenzene and Styrene | 92.3 |
| 2-Hydroxyethyl Methacrylate, Divinylbenzene and Styrene | 89.0 |
| Chloro(dimethyl)vinylsilane | 92.6 |

Figure 4A:
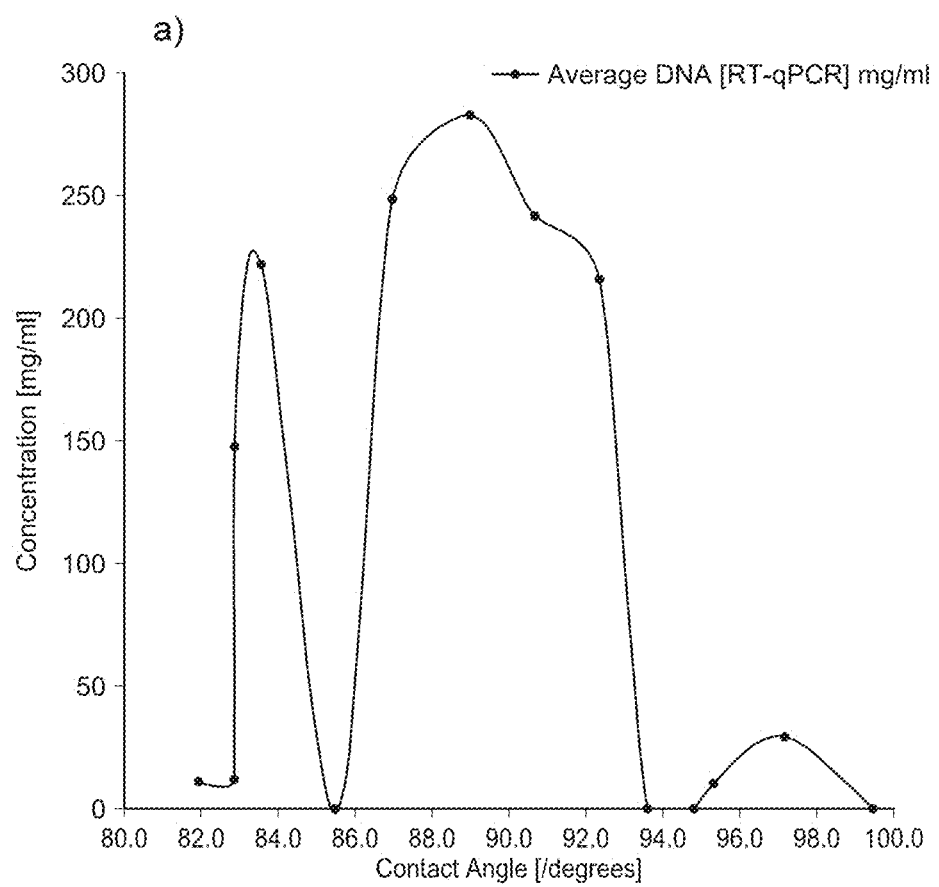
FIG. 4A shows the quantification of DNA in fractions as a function of surface wettability.
Figure 4B:
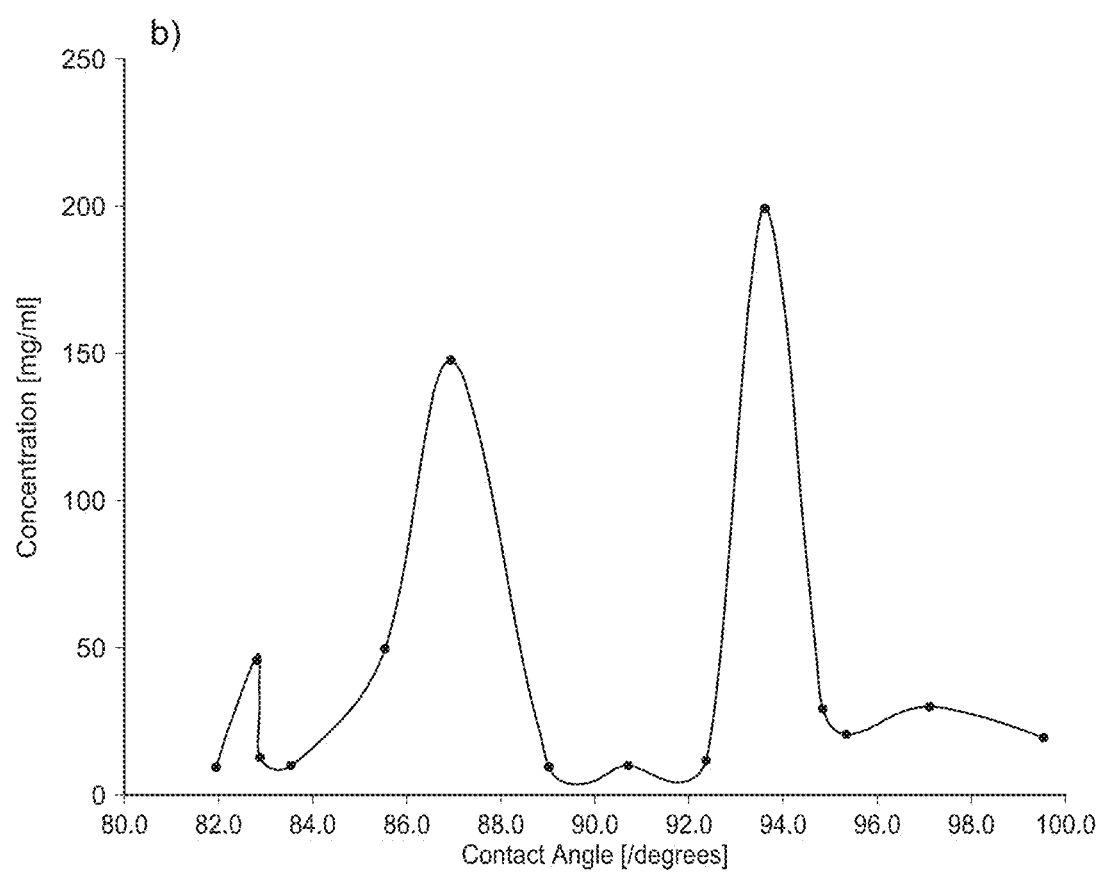
FIG. 4B shows the quantification of protein in fractions as a function of surface wettability.

FIGS. 4A and 4B show the quantification of DNA and protein in fractions as a function of surface wettability. Interestingly, the trends observed on bulk materials were well represented in the biological performance data. As wettability approaches 80°, DNA concentration is generally observed to increase while protein concentration is shown to be reduced. Remarkably, DNA and protein concentrations mirror each other in their inverse responses, giving good indication of which material is retained in the DEC. Significantly, there is a clear window of 80-94° surface wettability that facilitates the adsorption of both large and small proteins whilst also reducing DNA adhesion.

Biological Activity as a Function of Structural Variation

Physisorption of proteins is a complex process influenced by many factors related to electrostatic and hydrophobic interactions between substrate and molecule. The selective control of non-covalent interactions, such as hydrogen bonds, van der waals forces, π-π stacking, co-ordination and dispersive forces through appropriately functionalizing monomer units may be involved in selectively directing the adsorption/repulsion of biological species to a given substrate.

Figure 5:
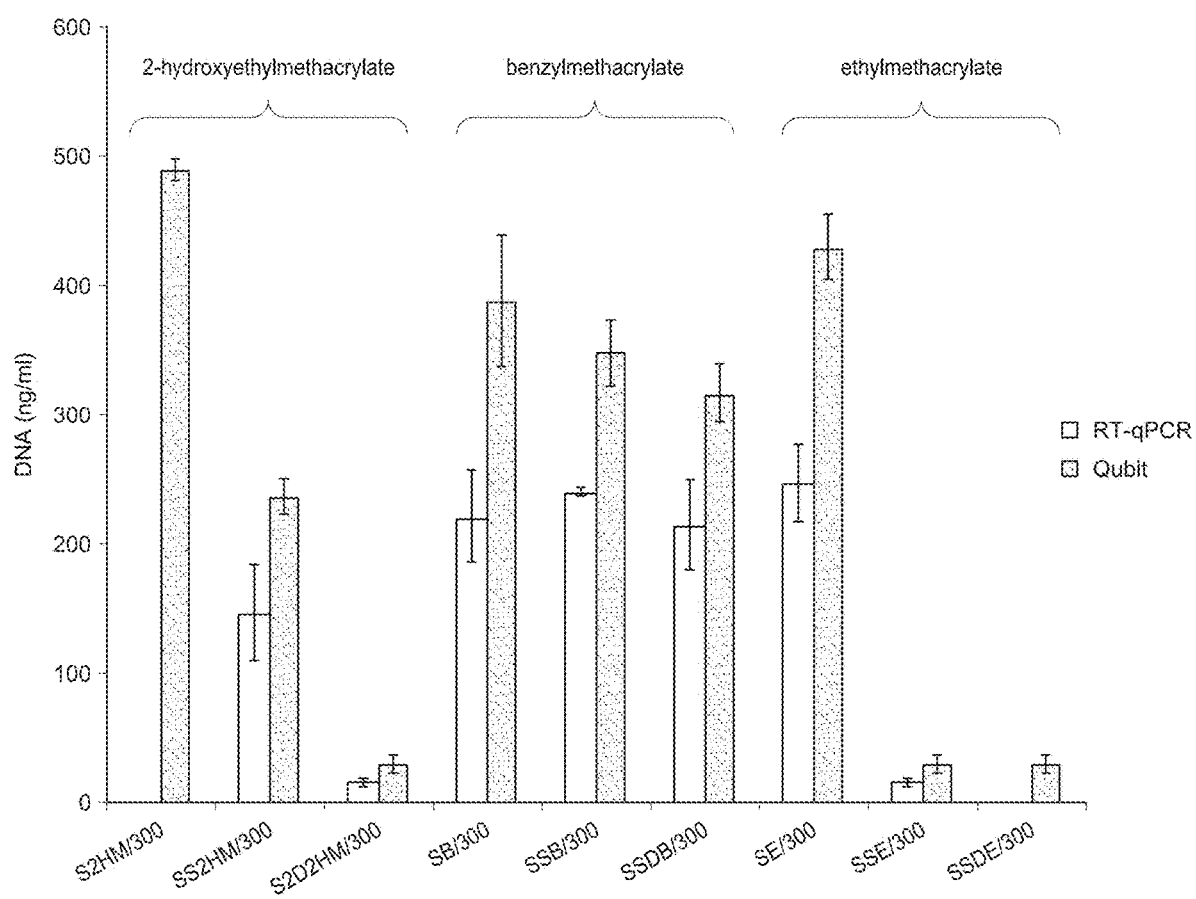
FIG. 5 shows DNA & protein concentrations in fractions collected from three derivatives of benzylmethacrylate studied in a range of polymeric systems.

Only samples containing a significant aromatic content perform well at simultaneously adsorbing protein and repelling DNA despite falling near or in the desired wettability range. For example, 4-vinylphenol, divinylbenzene and methacrylic acid presents a contact angle of 85.5°, which falls well within the optimal window. However, DNA seems to be retained on the column with high protein content collected in the DEC fraction. While aromatic containing systems such as [benzyl methacrylate], [benzyl methacrylate and styrene], [benzyl methacrylate, divinylbenzene and styrene], [2-hydroxyethyl methacrylate, divinylbenzene and styrene] seem to be better at distinguishing between the DNA and proteins. This is again exemplified by [ethyl methacrylate], which gives a contact angle of 87°, high DNA concentration but also a high protein content. FIG. 5 shows DNA & protein concentrations in fractions collected from three derivatives of benzylmethacrylate studied in a range of polymeric systems. Samples of silica-styrene (SS)/silica-styrene-divinylbenzene (SSD) modified with either 2-hydroxyethylmethacrylate (2HM), benzylmethacrylate (B) or ethyl methacrylate (E) were used and DNA was again extracted from blood lysate.

Here, the role of the aromatic substituent in DNA concentrations obtained from the column is clear, with all benzyl containing compounds shown to perform well. A direct surface modification of benzylmethacrylate alone gives a comparable performance to the more complex systems. In one embodiment, a contact angle between 80-90° and structural requirement of an aromatic is preferred for the simultaneous adsorption of proteins and repulsion of DNA.

Biological Activity as a Function of Active Surface Area

Modification of silica with polymer typically results in filling the pores with the desired material, essentially growing polymer brushes within the pores. As discussed earlier, the hydrodynamic radius should be of an appropriate size to enable analytes to enter and be retained by the pore. In this case, we have defined this as the active surface area. However, we acknowledge the active surface area is more accurately described as the pore size and the average interstitial spacing between particles in order to account for the size exclusion mechanism of the system.

In order to investigate the effect of active surface are in terms of polymer, 60 Å, 120 Å or 300 Å pore sizes were studied. DNA was eluted into 300 µl fractions using a flow rate of 100 µl/min, these fractions were used for DNA and protein quantification as previously described. It should also be noted that in each experiment the path length remains fixed.

TABLE 2

Pore Sizes and the Related Biological Function

| Pore Size | | |
|---|---|---|
| 60 Å | DNA (RT-qPCR) | — |
| | DNA (Qubit) | 48 |
| | Protein | 412 |
| 120 Å | DNA (RT-qPCR) | — |
| | DNA (Qubit) | 122 |
| | Protein | 452 |
| 300 Å | DNA (RT-qPCR) | 65 |
| | DNA (Qubit) | 37 |
| | Protein | <20 |

Table 2 shows that by increasing the active surface area the discrimination between DNA and proteins increases and DNA extraction efficiency is improved by virtue of the increasing DNA concentration and reducing protein content. Conversely, when surface area is increased, as a function of particle size i.e. active surface area contribution is less, we observe a reduction in DNA concentration (Table 3).

TABLE 3

Surface Area as a Function of Particle Size and Related Biological Performance

|  |  | no blood | Test 1 | Test 2 | Test 3 | Average |
|---|---|---|---|---|---|---|
| 15 micron | DNA (RT-qPCR) | 13 | 187 | 214 | 218 | 206 |
| 300 angstrom | DNA (Qubit) | <10 | 290 | 345 | 297 | 311 |
| 100 $m^2/g$ | Protein | 12 | 11 | 15 | 10 | 12 |
| 40-75 micron | DNA (RT-qPCR) | 1 | 160 | 169 | 156 | 162 |
| 300 angstrom | DNA (Qubit) | <10 | 272 | 269 | 255 | 265 |
| 108 $m^2/g$ | Protein | 10 | 10 | 14 | 11 | 12 |

The role of pore size is further demonstrated by decreasing the overall surface area of the sample whilst increasing the active surface area contribution. Table 4 compares the DNA extraction performance for 300 Å and 1000 Å pores sizes for 15 μm particles. The surface areas are 108 $m^2/g$ and 19 $m^2/g$ respectively. Thus, the increasing proportion of active surface area in the 1000 Å results in higher DNA concentrations from the same sample.

TABLE 4

Biological response for 300 Å and 1000 Å pores sizes for 15 μm particles. The surface areas are 108 $m^2/g$ and 19 $m^2/g$ respectively.

|  |  | no blood | Test 1 | Test 2 | Test 3 | Average |
|---|---|---|---|---|---|---|
| Pore Size | DNA (RT-qPCR) | 0 | 139 | 115 | 124 | 126 |
| 300 angstrom | DNA (Qubit) | 12 | 237 | 213 | 220 | 223 |
|  | Protein | 15 | 18 | 17 | 17 | 17 |
| Pore Size | DNA (RT-qPCR) | 0 | 134 | 140 | 144 | 139 |
| 1000 angstrom | DNA (Qubit) | 10 | 230 | 220 | 225 | 225 |
|  | Protein | 11 | 20 | 19 | 21 | 20 |

While the active surface area is involved in enabling the separation of DNA from protein, average interstitial spacing also plays a role. Here, the particle size plays a role in ensuring high volume of the sample comes into sufficient contact with the active surface area for separation to take place. Interstitial distance or average interstitial distance is proportional to particle size. Should this value be too large, then extraction efficiency will be reduced. Hence larger particles exhibit poorer performance characteristics. While it is difficult to separate the role of active surface area from the role of average interstitial distance, average interstitial distance/area is a factor in determining the efficiency of the extraction device and estimate the functioning region to be 0.2-1.5 μm and 12-24.5 μm² based on the dimensions of the samples studied.

Effect of Structural Uniformity on Downstream Processes (e.g. PCR)

As discussed earlier, any particle size stated for chromatography column is actually the mean value from a distribution of particle sizes, achieved practically by the manufacturer using automated sub-sieve sizing techniques. In reality a wide distribution of particles will lead to heterogeneity within the column, this can lead to an increase in variable path lengths the analyte molecules take through the column. As such uniformity is key in reducing inter-test variation. The effect of variable particle size is evident when comparing DNA extraction capability analyzed using qPCR of samples with uniformed size distribution against samples with high degree of heterogeneity. Table 5 shows the DNA extraction capability analyzed using qPCR for material with a >55% size distribution (Sample A) and 12.5% variation in size distribution (Sample B).

TABLE 5

DNA extraction capability analyzed using qPCR for material with a >55% size distribution (Sample A) and 12.5% variation in size distribution (Sample B).

|  |  | no blood | Test 1 | Test 2 | Test 3 | Average |
|---|---|---|---|---|---|---|
| Sample A | DNA (RT-qPCR) | 4 | 115 | 109 | 42 | 89 |
|  | DNA (Qubit) | <5 | 146 | 123 | 68 | 112 |
|  | Protein | <10 | 22 | 22 | 22 | 22 |
| Sample B | DNA (RT-qPCR) | 7 | 297 | 324 | 335 | 319 |
|  | DNA (Qubit) | <5 | 361 | 357 | 349 | 356 |
|  | Protein | <10 | <10 | <10 | <10 | <10 |

The results clearly illustrate the effect of increased variation in path length for analytes through the extraction device. A trend which is evident regardless of the sorbent material or its form factor, as described below. As such, uniformity is considered to be another factor in defining extraction performance. Surface area and active surface area are factors in defining performance characteristics. In one embodiment, the functioning region of average interstitial distance/area is preferably about 0.2-1.5 μm and 12-24.5 μm². Thus, dimensional uniformity is a factor in defining extraction performance.

Biological Activity as a Function of Surface Area, Pore Size and Average Interstitial Spacing In order to fully demonstrate the fundamental role of each embodiment described, sorbent material was generated in line with the described parameters. The biological performance of each material demonstrates the specific criteria of average interstitial spacing, appropriate polymer selection, pore size and active surface area in effective DNA-Extraction.

Defining Effective Surface Area
  Silica Particles
    15 urn Surface area 80-120 $m^2/g$
    Average pore size 300 Å/30 nm
    Pack 200 mg in columns/DECs=16-24 $m^2$ surface area in device
  Electro Spun Fibers
    Surface area of an fiber=$2\pi rl$
    Surface Area of Sorbent Material=$2\pi rl \times$number of fibers
    R=SA/$2\pi rl \times$number of fibers
    SA=16 $m^2$ (less spacing)-24 $m^2$ (more spacing)
    Assume 1% effective surface area=0.16 $m^2$ i.e. just the pores of a particle from the silica extracts
    1 cm contains ~50000 (200 nm) fibers will give 1 cm long square
    R=2.58/number of fibers to 381.9/number of fibers=400 m/200 nm=$2\times10E^9$ fibers
    Ø=5/number of fibers to 800/number of fibers
    $2.0\times10^9/1.0\times10^5$ (number of fibers required/number of fibers in 1 $cm^2$)=20000 number of sheets×200 nm=$4\times10^{-3}$ m path length
  Electro Spun Polymers
    Benzyl methacrylate nanofibers (0.2 g) produced in the manner described earlier were weighed into 5 ml syringes. Using manual pressure, fibers were compressed for 2 minutes to provide the calculated $4\times10^{-3}$ m path length. The sample was then heated at 40 degrees for 30 minutes and subsequently cooled slowly. Activation buffer (700 ul) was pumped through the system prior to adding 80 ul of lysate.

Figure 7:
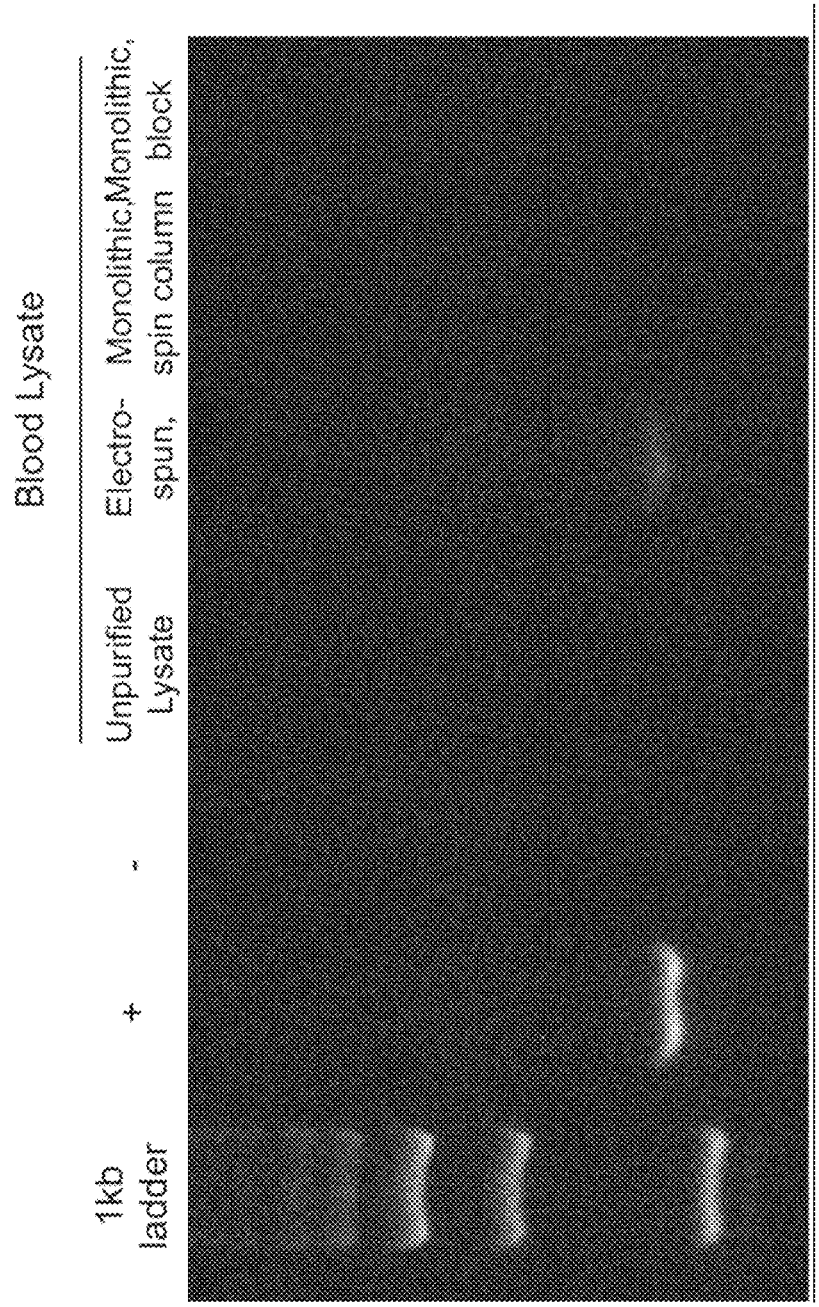
FIG. 7 shows an agarose gel image of PCR products from eluents collected from electro spun polymers, monolithic columns and a monolithic block. '+' is PCR mix with genomic DNA added, '−' PCR mix with water added. N.b some bands are difficult to see partly due to display quality.

The fluid was pushed through the system and the eluents retained for analysis. FIG. 7 shows the typical performance of syringes prepared in this manner.

Figure 6:
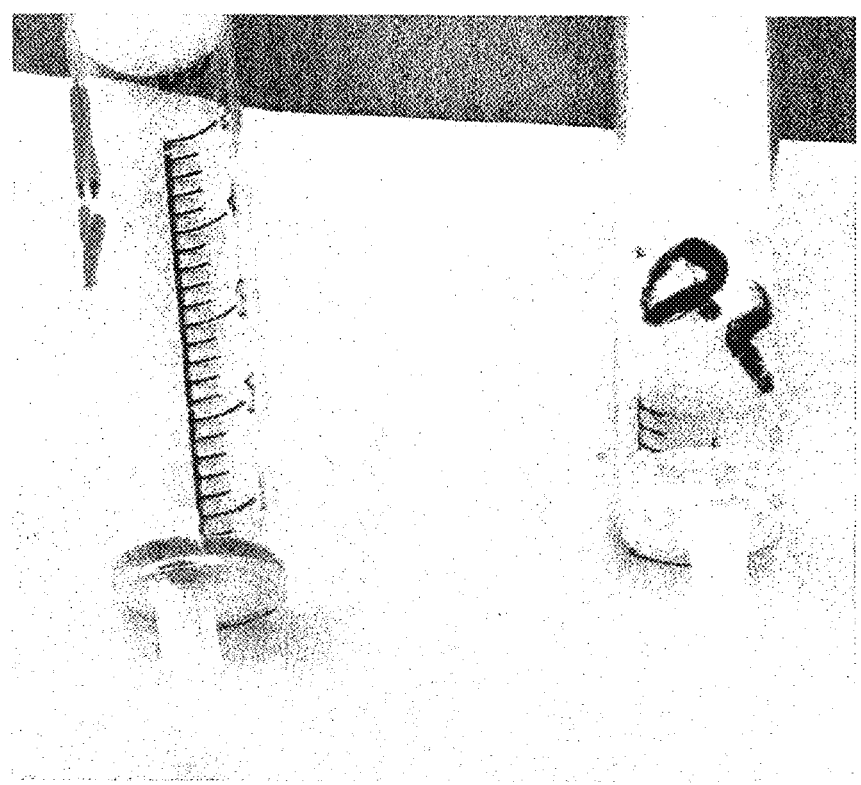
FIG. 6 shows examples of columns. Left; an example where average interstitial spacing/surface area falls outside the specified criteria, lysate is visible passing straight through the column right; an example where the average interstitial spacing/surface area has been met, no lysate is evident passing substantially through the column.

In all instances where the appropriate path length was not met (to provide the appropriate average interstitial spacing and surface area) extraction for PCR was not successful (FIGS. 6 and 7).

Figure 8:
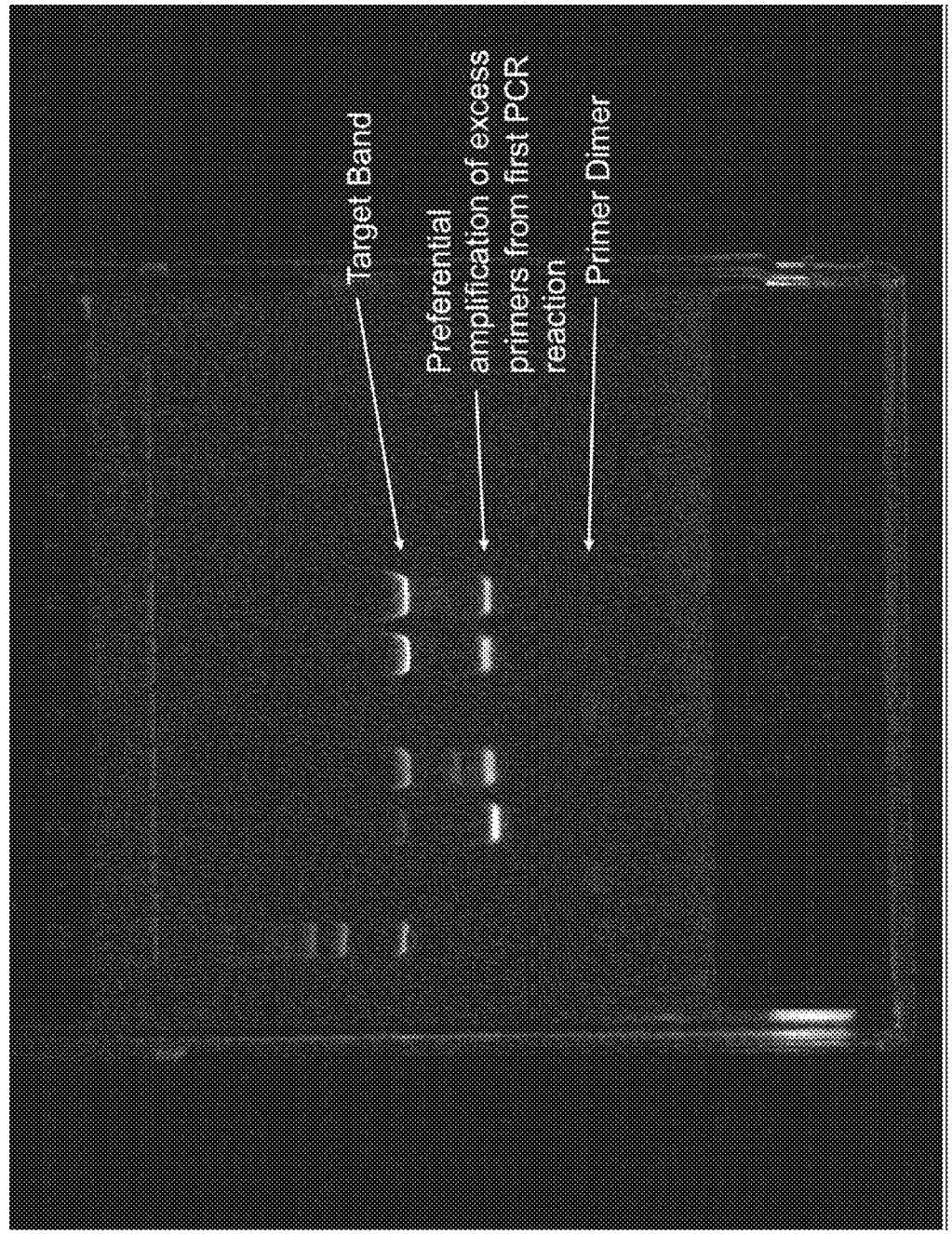
FIG. 8 shows an agarose gel image of PCR products from eluents collected from electro spun polymers, monolithic columns and a monolithic block. '+' is PCR mix with genomic DNA added, '−' PCR mix with water added. N.b some bands are difficult to see due to display quality.

Flow through testing of monolith series within spin columns and within fused-silica capillaries with pre-treatment, glass pipettes with pre-treatment, plastic syringes and glass vials without pre-treatment was carried out. Here, 350 μl of activation buffer was added and spun in the centrifuge for 1 minute. The spin speed was increased to 5000 rpm to elute the buffer. 80 μl of blood lysate was added to the columns in which the activation buffer had passed through; these were then spun at 5000 rpm for 1 minute. The eluents were collected and analyzed for their biological constituents by gel electrophoresis (FIG. 8).

Example Summary

Average interstitial spacing for silica (15 μm, 300 Å) was calculated to be 6.95 μm assuming uniform packing. Average interstitial spacing is also a function of surface area and the ratio between the two parameters. By fixing, monomer unit and defining surface area (as above), new architectures have been formed with the appropriate dimensions to extract DNA from blood lysate. As shown in Table 6, examples having average interstitial spacing below about 6 μm or above about 23 μm fail to purify DNA to an acceptable level for analysis.

TABLE 6

Dimensions of tested examples

| Average interstitial Spacing | Silica Particles ([DNA] ng/mL) | Monolithic Columns ([DNA] ng/mL) | Electro Spun Mats ([DNA] ng/mL) |
|---|---|---|---|
| 23.13-35.48 μm | Not quantified | Not quantified | Not quantified |
| 6.25-23.13 μm | 2017 (15 μm, 300 Å) | 9.95 | 25.72 |
| 0-6.25 μm | Not available commercially | Not quantified (bulk monolith) | Not quantified |

The calculated ranges for average interstitial spacing are based on accurate silica average diameter values and measured values for monolith and electro spun materials. "Not quantified" refers to RT-PCR failure, typically due to too much PCR inhibition from high protein concentration or too low DNA concentration obtained from the extraction device.

Comparative Examples

Particle Distribution/Pore Radius

Figure 9:
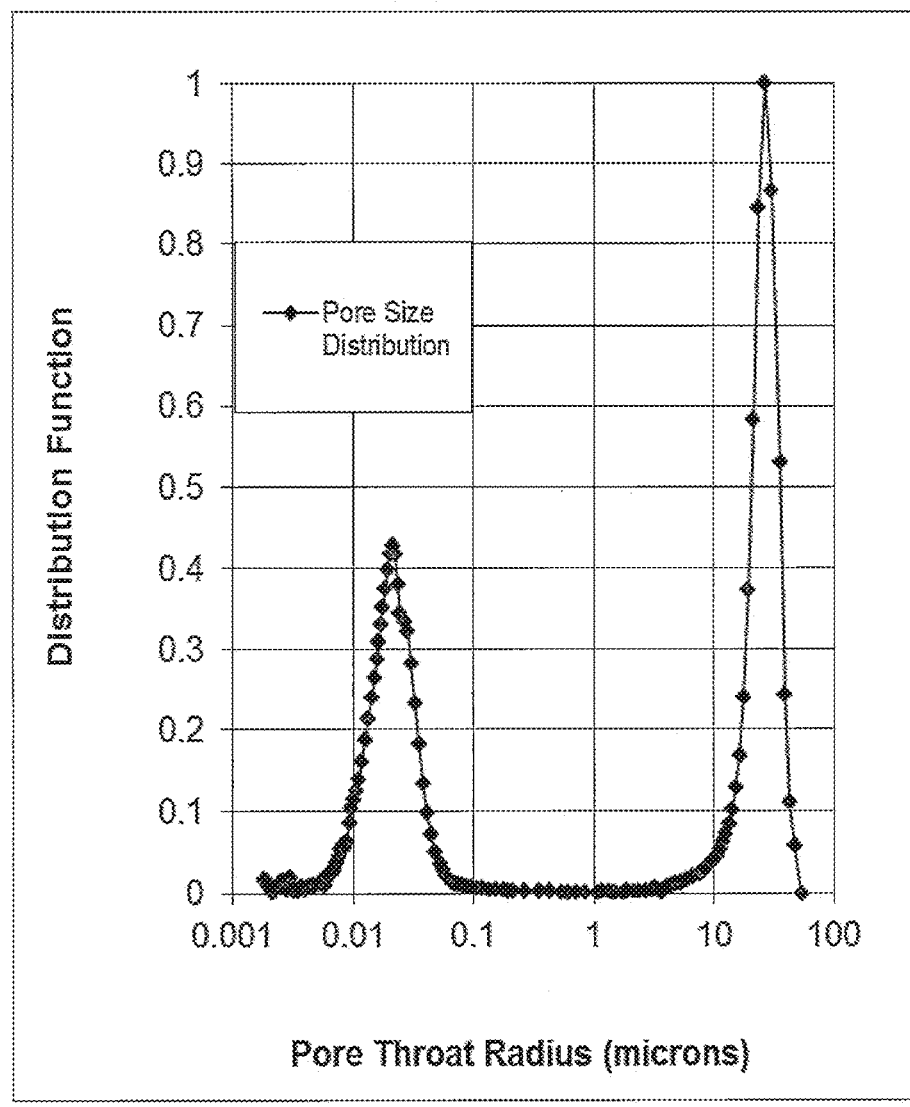
FIG. 9 shows a graph demonstrating wide distribution of particles.
Figure 10:
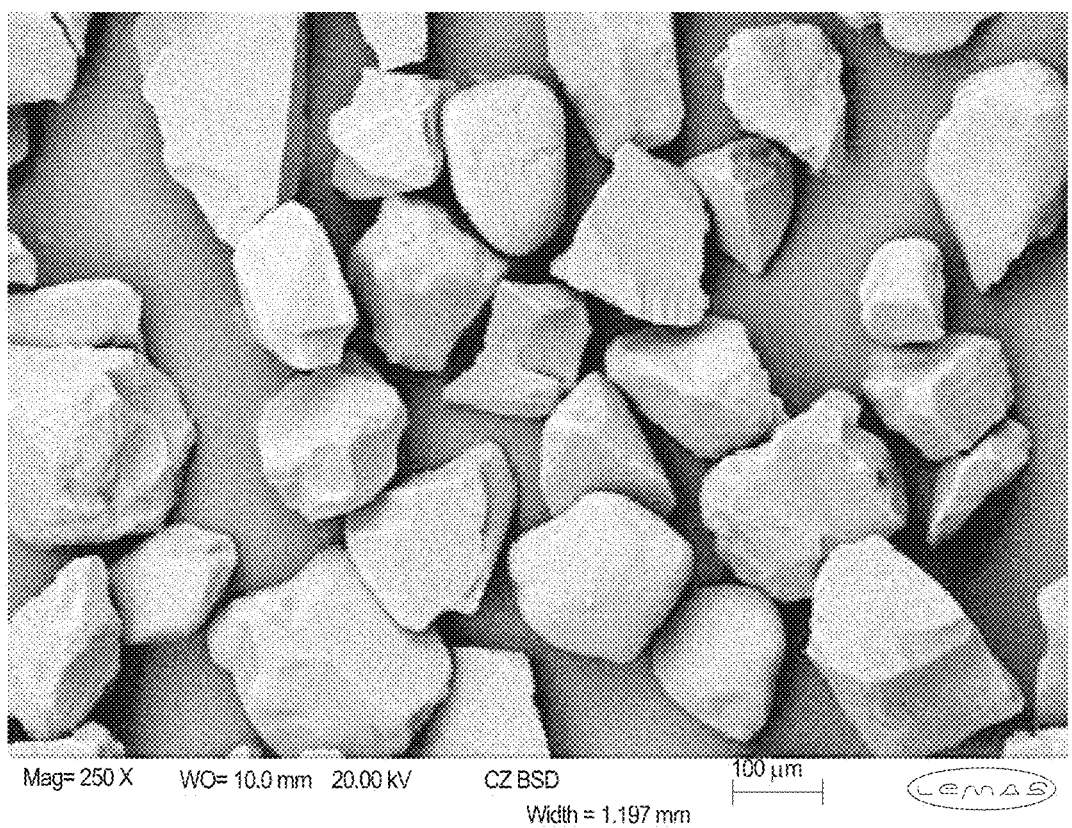
FIG. 10 shows an electro micrograph image demonstrating wide distribution of particles in a extraction material representing comparative examples.

A wide distribution of particle sizes and pore radius (FIGS. 9 and 10) will lead to heterogeneity within the column and as such, an increase in variable path lengths the analyte molecules can take through the column. DNA-Extraction efficiency is severely impaired in such a case and often results in high protein contamination.

Surface Area

Active surface area plays a significant role in DNA-Extraction efficiency. As described earlier, we understand the optimum range, in at least some embodiments, to be between 0.1 m² - 150 m². At least in some embodiments, the discrete combination of the described parameters each falling within the specified range may play roles in determining the ability of the sorbent material to extract DNA from blood lysate.

Measured surface area of a poorly extracting silica based material falls within this range. However, evident from previously presented data, it is the specific combination of surface area in conjunction with pore size, polymer system and average interstitial spacing that provides the DNA-Extraction mechanism. The surface areas of some tested samples are provided in Table 7.

TABLE 7

Surface area of tested samples
Sample A Surface Area 58.48 m²/g (BET Surface Area)
80.24 m²/g (Langmuir Surface Area)

Examples

Synthesis of Porous Silicon Wafers

Figure 11:
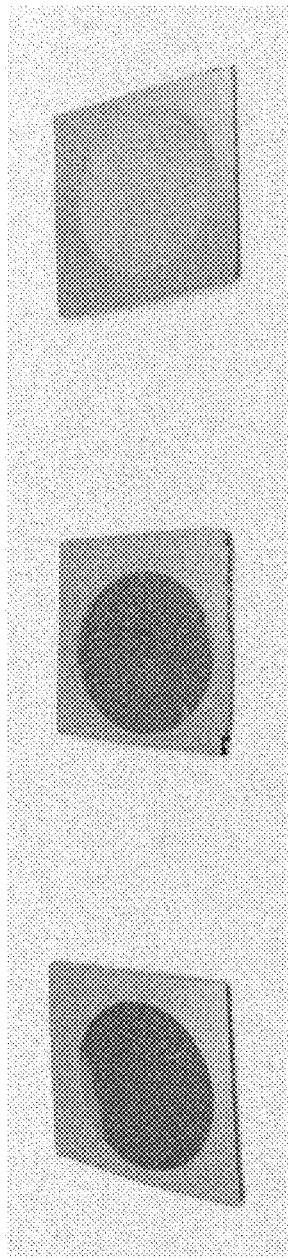
FIG. 11 shows bare porous silicon (left), silane modified porous silicon (center), and porous silicon modified with benzyl methacrylate (right).
Figure 12:
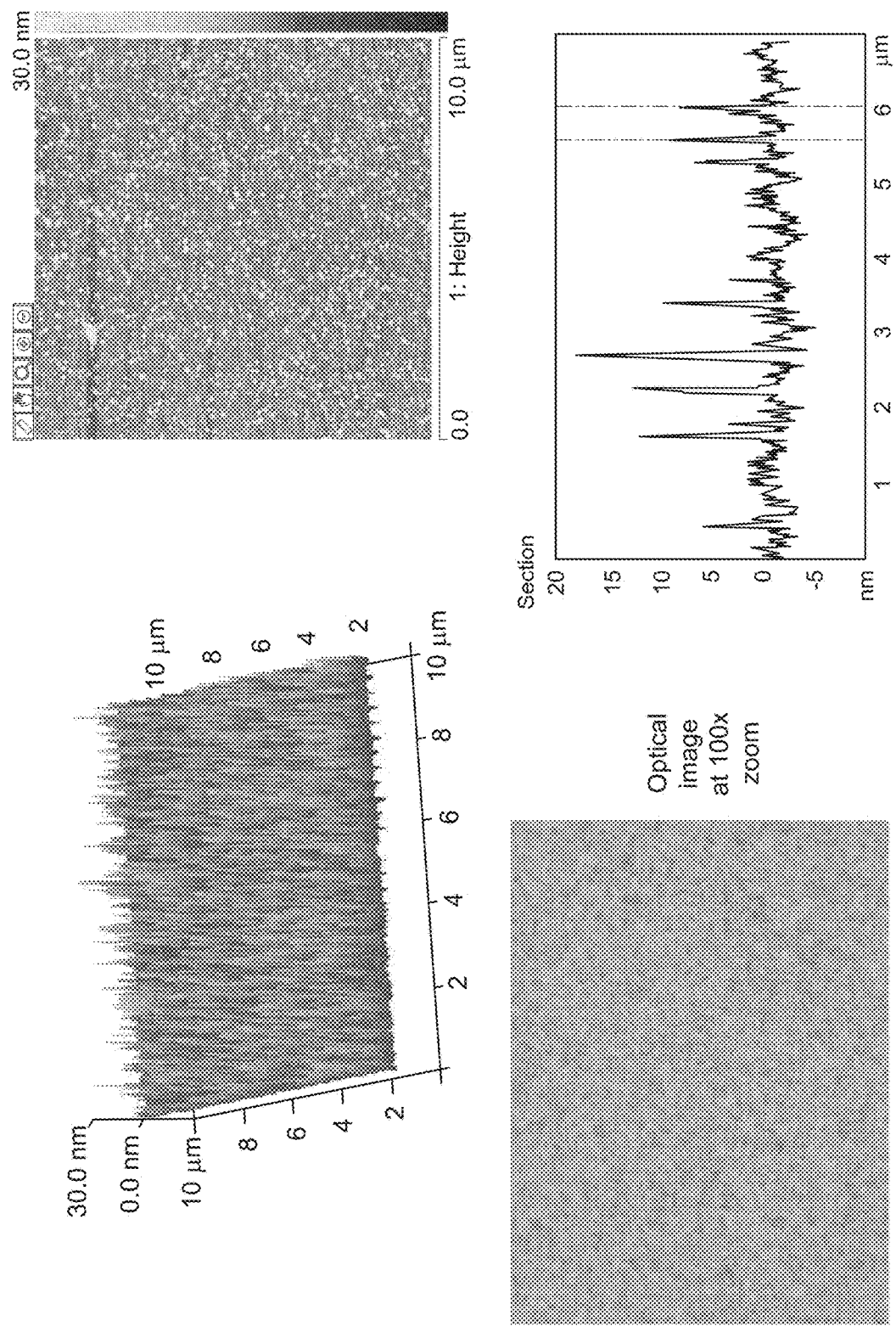
FIG. 12 shows AFM analysis of bare porous silicon.

Galvanostaticanodisation of p-Si (100) wafer formed porous silicon layers. This was performed using a cell containing a 1:1 v/v solution of 48% aqueous HF and ethanol solution. The electrochemical cell was composed from PTFE and had a circular cross-section. The silicon wafer was sealed to the base using a Teflon coated Viton™ O-ring. The counter electrode was composed of tungsten wire coiled into a loop; this provided a uniform current distribution. A high current density (5 min at 500 mA cm²) was used to produce a layer of porous silicon. FIG. 11 shows bare porous silicon (left), silane modified porous silicon (center), and porous silicon modified with benzyl methacrylate (right), and FIG. 12 shows AFM analysis of bare porous silicon.

Figure 13:
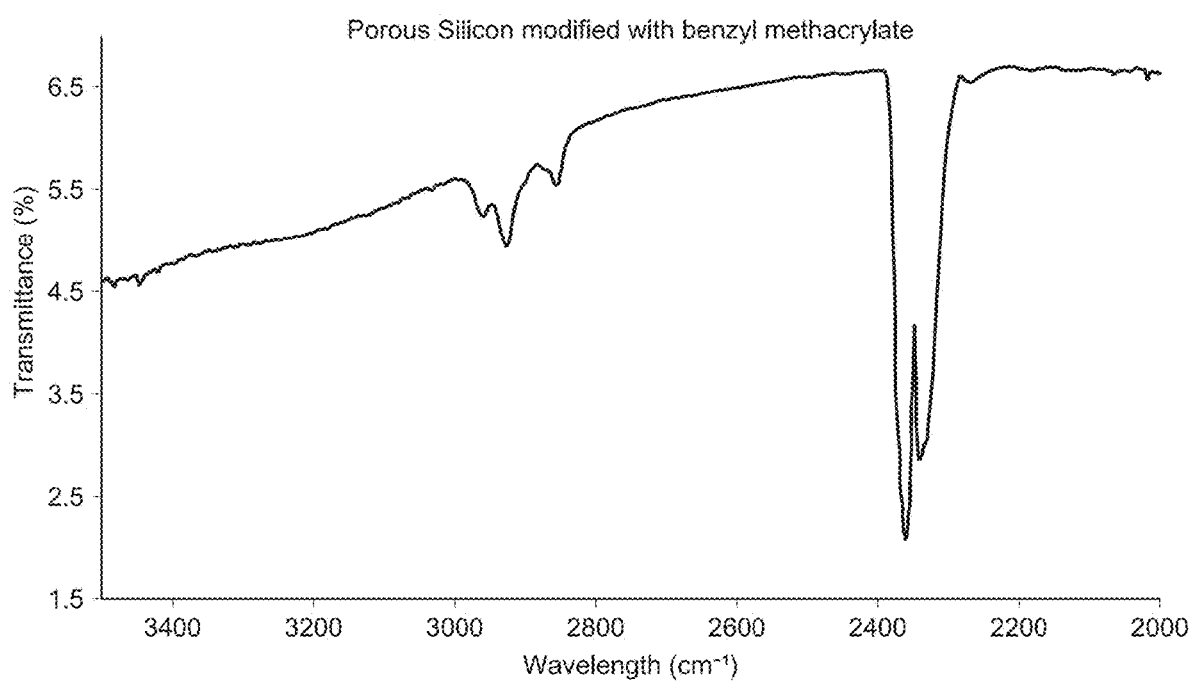
FIG. 13 shows FT-Ir spectra of porous silicon modified with benzyl methacrylate (3500-2000 $cm^{-1}$ region).

FIG. 13 shows FT-Ir spectra of porous silicon modified with benzyl methacrylate (3500-2000 cm$^{-1}$ region). The restrictive effect that polymer immobilization has on vibration and therefore the vibrational modes of functional groups was evident in the spectra and resulted in a number of bands attributed to C—H vibrations shifting to lower wavenumbers. The aromatic C—H vibration of the benzyl group is evident and was observed to have shifted from 3066 cm$^{-1}$ to ~2950 cm$^{-1}$. Note—the strong band observed at 2300 cm$^{-1}$ is attributed to the atmospheric presence of $CO_2$.

Silica Particles, 15 Micron, 300 Å Pore Size

300 Å Silica (2.20 g) was dried for 3 h at 200° C. in vacuo followed by overnight at room temperature under house vacuum. A 50 mL round bottom flask and stirrer were dried in the oven overnight.

300 Å Silica (2.15 g) was suspended in a 5% solution of dimethylvinylchlorosilane in trifluorotoluene (6 mL) and stirred for 15 min at 110° C. The mixture was allowed to cool to room temperature and the stirring stopped. Once the silica had settled, the liquid was pipetted off and replaced with fresh 5% solution of dimethylvinylchlorosilane in trifluorotoluene (6 mL). The mixture was then heated back to 110° C. and stirred for 15 min. This method was performed a further time before cooling to room temperature and filtering. The silica was collected via vacuum filtration and was washed with acetone (5×10 mL) and water (5×10 mL). The silica was air-dried for 30 min at room temperature before drying in vacuo for 3 h while cautiously raising the temperature to 120° C. to avoid any loss of silica.

To a stirred solution of sodium stearate (140 mg) in water (10 mL) was added silica (~2 g), benzylmethacrylate (0.53 mL) and potassium peroxodisulfate (5 mg). The polymerization was conducted at 95° C. for 4 h. The mixture was cooled to room temperature and filtered. The resulting silica was washed with DMF (5×10 mL), ethanol (5×10 mL) and water (5×10 mL) before being air-dried for 30 min at room temperature. The silica was finally dried in vacuo for 3 h while cautiously raising the temperature to 80° C., and changing the trap when saturated with water. 300 Å silianized silica-benzylmethacrylate (2.21 g) was obtained as a white solid.

Figure 14:
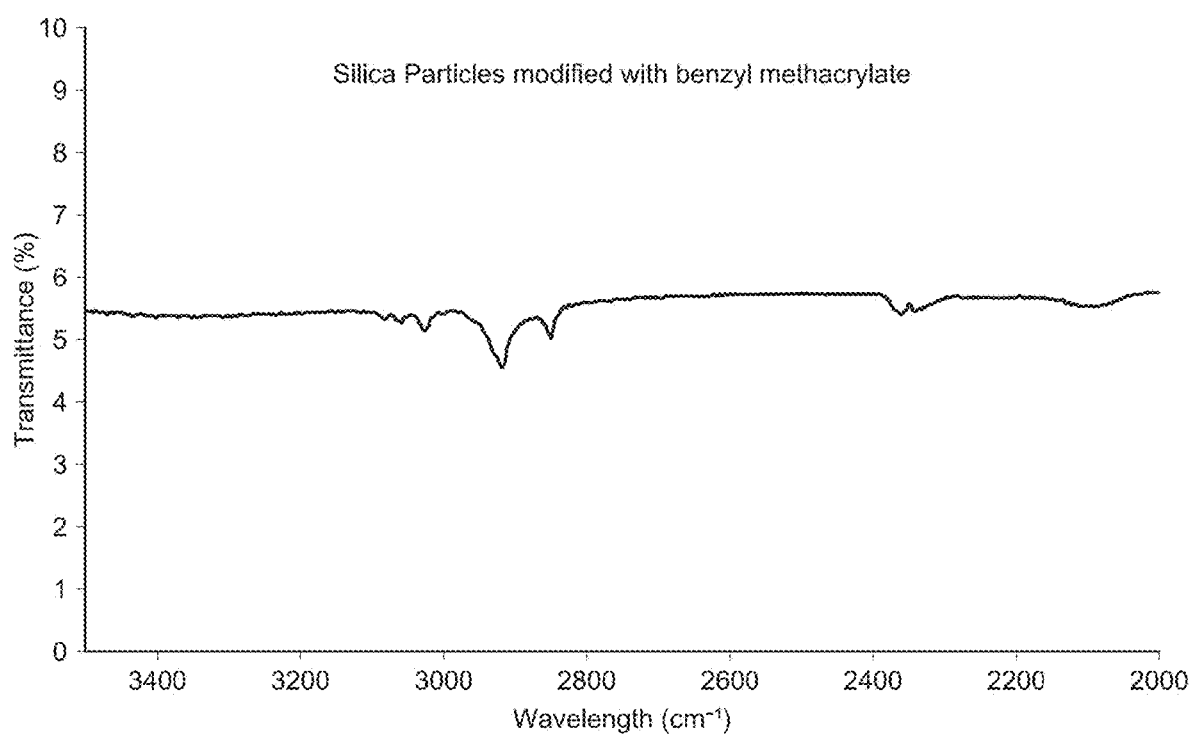
FIG. 14 shows FT-Ir spectra of silica particles modified with benzyl methacrylate (3500-2000 $cm^{-1}$ region).

FIG. 14 shows FT-Ir spectra of silica particles modified with benzyl methacrylate (3500-2000 cm$^{-1}$ region). The restrictive effect that polymer immobilization has on vibration and therefore the vibrational modes of functional groups was evident in the spectra and resulted in a number of bands attributed to C—H vibrations shifting to lower wavenumbers. The aromatic C—H vibration of the benzyl group is evident and was observed to have shifted from 3066 cm$^{-1}$ to ~2900 cm$^{-1}$.

Additional Examples of Syntheses of SilicaParticles

Polymerization with 300 Å, 15 μm (Silianized Silica)

To a stirred solution of sodium stearate (67 mg) in water (4.8 mL) was added silica, the monomer and potassium peroxodisulfate (2.4 mg). The polymerization was conducted at 95° C. for 4 h. The mixture was cooled to room temperature and filtered. The resulting silica was washed with DMF (5×5 mL), ethanol (5×5 mL) and water (5×5 mL) before being air-dried for 30 min at room temperature. The silica was finally dried in vacuo for 3 h while cautiously raising the temperature to 80° C., and changing the trap when saturated with water.

Synthesis of 300 Å, 15 μm (Silianized Silica-Styrene)

300 Å Silica (2.20 g) was dried for 3 h at 200° C. in vacuo followed by overnight at room temperature under house vacuum. A 50 mL round bottom flask and stirrer were dried in the oven overnight.

300 Å Silica (2.15 g) was suspended in a 5% solution of dimethylvinylchlorosilane in trifluorotoluene (6 mL) and stirred for 15 min at 110° C. The mixture was allowed to cool to room temperature and the stirring stopped. Once the silica had settled, the liquid was pipetted off and replaced with fresh 5% solution of dimethylvinylchlorosilane in trifluorotoluene (6 mL). The mixture was then heated back to 110° C. and stirred for 15 min. This method was performed a further time before cooling to room temperature and filtering. The silica was collected via vacuum filtration and was washed with acetone (5×10 mL) and water (5×10 mL). The silica was air-dried for 30 min at room temperature before drying in vacuo for 3 h while cautiously raising the temperature to 120° C. to avoid any loss of silica.

To a stirred solution of sodium stearate (140 mg) in water (10 mL) was added silica (~2 g), styrene (0.52 mL) and potassium peroxodisulfate (5 mg). The polymerization was conducted at 95° C. for 4 h. The mixture was cooled to room temperature and filtered. The resulting silica was washed with DMF (5×10 mL), ethanol (5×10 mL) and water (5×10 mL) before being air-dried for 30 min at room temperature. The silica was finally dried in vacuo for 3 h while cautiously raising the temperature to 80° C., and changing the trap when saturated with water. 300 Å silianized silica-styrene (1.68 g) was obtained as a white solid.

Synthesis of 300 Å, 15 μm Silianized Silica-Divinylbenzene

300 Å Silica (1.20 g) was dried for 3 h at 200° C. in vacuo followed by overnight at room temperature under house vacuum. A 50 mL round bottom flask and stirrer were dried in the oven overnight.

300 Å Silica (1.15 g) was suspended in a 5% solution of dimethylvinylchlorosilane in trifluorotoluene (3 mL) and stirred for 15 min at 110° C. The mixture was allowed to cool to room temperature and the stirring stopped. Once the silica had settled, the liquid was pipetted off and replaced with fresh 5% solution of dimethylvinylchlorosilane in trifluorotoluene (3 mL). The mixture was then heated back to 110° C. and stirred for 15 min. This method was performed a further time before cooling to room temperature and filtering. The silica was collected via vacuum filtration and was washed with acetone (5×5 mL) and water (5×5 mL). The silica was air-dried for 30 min at room temperature before drying in vacuo for 3 h while cautiously raising the temperature to 120° C. to avoid any loss of silica.

To a stirred solution of sodium stearate (70 mg) in water (5 mL) was added silica (~1 g), divinylbenzene (0.38 mL) and potassium peroxodisulfate (2.5 mg). The polymerization was conducted at 95° C. for 4 h. The mixture was cooled to room temperature and filtered. The resulting silica was washed with DMF (5×5 mL), ethanol (5×5 mL) and water (5×5 mL) before being air-dried for 30 min at room temperature. The silica was finally dried in vacuo for 3 h while cautiously raising the temperature to 80° C., and changing the trap when saturated with water. 300 Å silianized silica-divinylbenzene (1.00 g) was obtained as a white solid.

Synthesis of 300 Å, 15 μm (silianized silica-2-hydroxyethyhnethacrylate)

300 Å Silica (1.20 g) was dried for 3 h at 200° C. in vacuo followed by overnight at room temperature under house vacuum. A 50 mL round bottom flask and stirrer were dried in the oven overnight.

300 Å Silica (1.15 g) was suspended in a 5% solution of dimethylvinylchlorosilane in trifluorotoluene (3 mL) and stirred for 15 min at 110° C. The mixture was allowed to cool to room temperature and the stirring stopped. Once the silica had settled, the liquid was pipetted off and replaced with fresh 5% solution of dimethylvinylchlorosilane in trifluorotoluene (3 mL). The mixture was then heated back to 110° C. and stirred for 15 min. This method was performed a further time before cooling to room temperature and filtering. The silica was collected via vacuum filtration and was washed with acetone (5×5 mL) and water (5×5 mL). The silica was air-dried for 30 min at room temperature before drying in vacuo for 3 h while cautiously raising the temperature to 120° C. to avoid any loss of silica.

To a stirred solution of sodium stearate (70 mg) in water (5 mL) was added silica (~1 g), 2-hydroxyethylmethacrylate (0.33 mL) and potassium peroxodisulfate (2.5 mg). The polymerization was conducted at 95° C. for 4 h. The mixture was cooled to room temperature and filtered. The resulting silica was washed with DMF (5×5 mL), ethanol (5×5 mL) and water (5×5 mL) before being air-dried for 30 min at room temperature. The silica was finally dried in vacuo for 3 h while cautiously raising the temperature to 80° C., and changing the trap when saturated with water. 300 Å silianized silica-2-hydroxyethylmethacrylate (1.00 g) was obtained as a white solid.

Mixed Particle Sizes

A mixture of silica particles were prepared by firstly modifying two separate batches of materials with complimentary or identical polymer systems, e.g. using styrene and 2-hydroxyethylmethyl methacrylate monomer systems respectively in certain embodiments, but not limited to. Mixtures of particles at a desired ratio may enable compositions to be tailored by ratio of mass composition in order to ascertain extraction properties according to the sample type being extracted.

Modification of a Silicon Surfaces

Silicon chips (bulk and porous, 1 cm$^2$) were dried for 3 h at 200° C. in vacuo followed by overnight at room temperature under house vacuum. A 50 mL round bottom flask and stirrer were dried in the oven overnight.

Silica chips (1 cm$^2$) were suspended in a 5% solution of dimethylvinylchlorosilane in trifluorotoluene (12 mL) and stirred for 15 min at 110° C. The mixture was allowed to cool to room temperature and the stirring stopped. Once the silica had settled, the liquid was pipetted off and replaced with fresh 5% solution of dimethylvinylchlorosilane in trifluorotoluene (12 mL). The mixture was then heated back to 110° C. and stirred for 15 min. This method was performed a further time before cooling to room temperature and filtering. The silica was collected via vacuum filtration and was washed with acetone (5×20 mL) and water (5×20 mL). The silica was air-dried for 30 min at room temperature before drying in vacuo for 3 h while cautiously raising the temperature to 120° C.

To a stirred solution of sodium stearate (280 mg) in water (20 mL), styrene (1.04 mL), divinylbenzene (128 μL), 2-hydroxyethylmethacrylate (120 μL) and potassium peroxodisulfate (10 mg) were added. The silica chip was added to the solution. The polymerization was conducted at 95° C. for 4 h. The mixture was cooled to room temperature and filtered. The resulting silica was washed with DMF (5×20 mL), ethanol (5×20 mL) and water (5×20 mL) before being air-dried for 30 min at room temperature. The silica was finally dried in vacuo for 3 h while cautiously raising the temperature to 80° C., and changing the trap when saturated with water.

Electrospun Mats

Polyvinylalcohol (PVA)

A 10% wt. PVA (mw 89,000-98,000) solution was pumped towards aluminum foil taped to a copper rod. The distance between the needle and collector was 16 cm with an applied voltage of 20 kV. The flow rate of the polymer solution was 0.075 ml/h. Environmental conditions: 19% R.H., 20.3° C.

Polybenzylmethacrylate (P(BzMA))

Figure 15A:
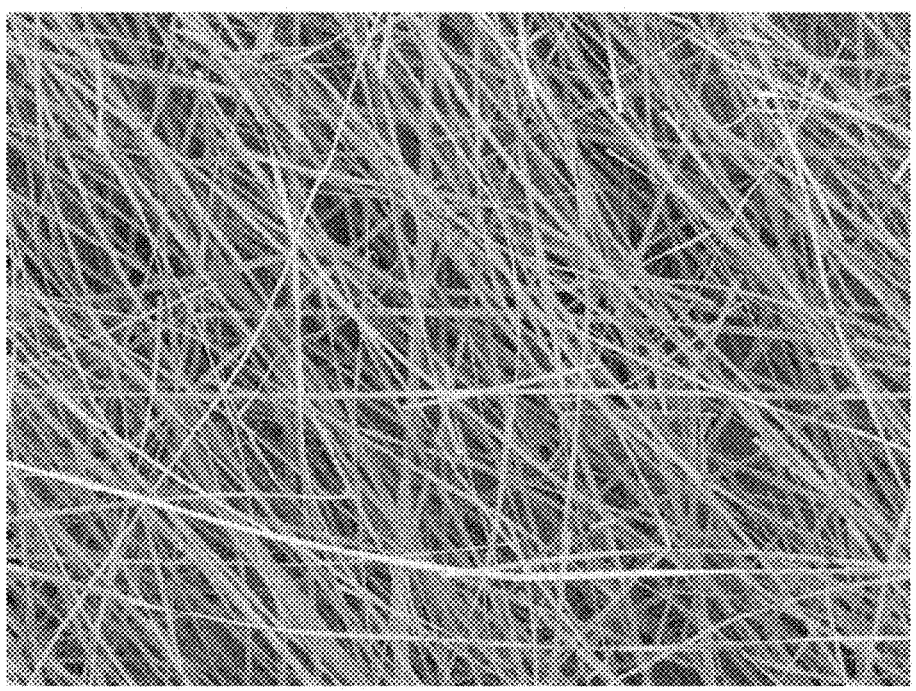
FIG. 15A shows SEM images of electro spun fibers of poly benzyl methacrylate. The SEM magnification is 180×.
Figure 15B:
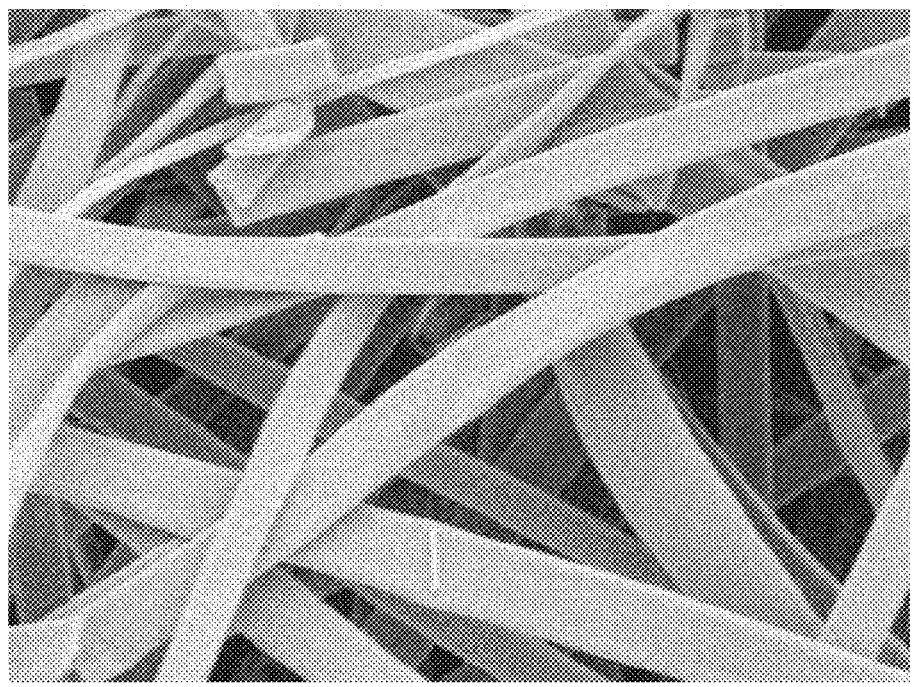
FIG. 15B shows SEM images of electro spun fibers of poly benzyl methacrylate. The SEM magnification is 2.01 kx.

A 37.5% wt. P(BzMA) in THF solution was pumped towards aluminum foil taped to a copper rod. The distance between the needle and collector was 10 cm with an applied voltage of 20 kV. The flow rate of the polymer solution was 0.05 ml/min. Environmental conditions: 21% R.H., 20.6° C. FIGS. 15A-C show optical images of an electrospun mat of polybenzylmethacrylate (P(BzMA)).

Pore size in this instance is considered analogous to average interstitial spacing while surface area can be calculated from the fiber size as shown previously. While it is difficult to separate the role of active surface area from the role of average interstitial distance, we understand average interstitial distance/area to be a factor in determining the efficiency of the extraction device. In general, the average interstitial distance may be greater than about 10 nm. In a variation, the average interstitial distance is less than about 12 microns.

Porous Polybenzylmethacrylate Fibers

At 17.5% w/w polymer/acetone the solution was prepared and left overnight in water at room temperature. Alternatively, 2 cm$^2$ square of the fiber mat on foil was treated with mild acid (1 M ethanoic acid), a 50:50 combination of ethanol and water, a 50:50 combination of methanol and water, in water at 40° C.

Synthesis of Novel Monomer Units

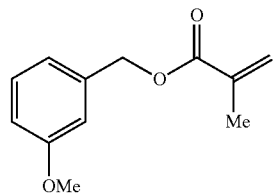

Anisolemethyl methacrylate

To a stirred solution of methacrylic acid (169 mg, 167 μL, 1.96 mmol), 3-methoxybenzyl alcohol (271 mg, 244 μL, 9.16 mmol) and 4-(dimethylamino)pyridine (311 mg, 2.55 mmol) in anhydrous dichloromethane (12 mL) was added N-(3-dimethylaminopropyl)-N'-ethylcarbodiimide hydrochloride (0.52 g, 2.75 mmol) and stirring was continued overnight. The solution was washed with saturated aqueous NaHCO$_3$ (10 mL), water (10 mL) and saturated brine (10 mL), dried (MgSO$_4$) and concentrated to give a viscous oil. This material was purified using a Biotage Isolera automated chromatography system under normal phase conditions (silica column, gradient of 2→16% diethyl ether in petrol) with detection at 254 nm to afford anisolemethyl methacrylate (121 mg, 30%) as a colorless oil. Rf 0.33 (petrol—diethyl ether, 92:8 v/v).

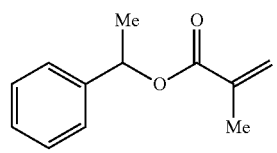

Phenylethanol methacrylate

To a stirred solution of phenylethanol (0.50 g, 0.50 mL, 4.09 mmol) and triethylamine (1.24 g, 1.71 mL, 12.27 mmol) in anhydrous dichloromethane (5 mL) at 0° C. was added methacryloyl chloride (470 mg, 436 μL, 4.50 mmol) dropwise, and stirring was continued for 30 min during which time the mixture was allowed to warm to room temperature. Water (25 mL) was added and the mixture was extracted with dichloromethane (3×25 mL). The combined organic layers were dried (MgSO$_4$) and concentrated to give a yellow oil (0.74 g). This material was purified using a Biotage Isolera automated chromatography system under normal phase conditions (silica column, gradient of 12→100% diethyl ether in petrol) with detection at 254 nm to afford phenylethanol methacrylate (0.80 g, quantitative) as a colorless oil. Rf 0.61 (petrol—diethyl ether, 3:1 v/v).

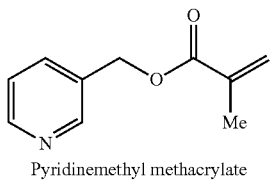

Pyridinemethyl methacrylate

To a stirred solution of methacrylic acid (0.72 g, 0.71 mL, 8.33 mmol) and 3-pyridinemethanol (1.00 g, 0.89 mL, 9.16 mmol) in anhydrous dichloromethane (23 mL) at 0° C. were added N-(3-dimethylaminopropyl)-N'-ethylcarbodiimide hydrochloride (2.23 g, 11.66 mmol) triethylamine (1.05 g, 1.45 mL, 10.41 mmol) and 4-(dimethylamino)pyridine (102 mg, 0.83 mmol), and stirring was continued overnight during which time the mixture was allowed to warm to room temperature. The solution was diluted with dichloromethane (50 mL) and was washed with saturated aqueous NaHCO$_3$ (30 mL), water (2×30 mL) and saturated brine (30 mL), dried (MgSO$_4$) and concentrated to give a viscous oil. This material was purified using a Biotage Isolera automated chromatography system under normal phase conditions (silica column, gradient of 12→100% ethyl acetate in petrol) with detection at 254 nm to afford pyridinemethyl methacrylate (1.06 g, 72%) as a colorless oil. Rf 0.38 (petrol—ethyl acetate, 1:1 v/v).

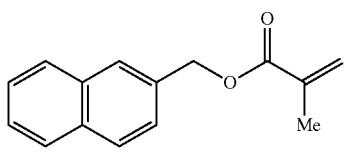

Naphthalenemethyl methacrylate

To a stirred solution of methacrylic acid (0.72 g, 0.71 mL, 8.33 mmol) and 1-naphthalenemethanol (1.45 g, 9.16 mmol) in anhydrous dichloromethane (23 mL) at 0° C. were added N-(3-dimethylaminopropyl)-N'-ethylcarbodiimide hydrochloride (2.23 g, 11.66 mmol) triethylamine (1.05 g, 1.45 mL, 10.41 mmol) and 4-(dimethylamino)pyridine (102 mg, 0.83 mmol), and stirring was continued overnight during which the mixture was allowed to warm to room temperature. The solution was diluted with dichloromethane (50 mL) and was washed with saturated aqueous NaHCO$_3$ (30 mL), water (2×30 mL) and saturated brine (30 mL), dried (MgSO$_4$) and concentrated to give a viscous oil. This material was purified using a Biotage Isolera automated chromatography system under normal phase conditions (silica column, gradient of 2→20% ethyl acetate in petrol) with detection at 254 nm to afford napthalenemethylmethacrylate (1.28 g, 68%) as a colorless oil. Rf 0.53 (petrol—ethyl acetate, 9:1 v/v).

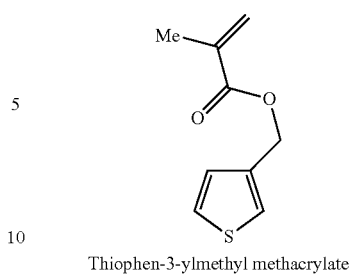

Thiophen-3-ylmethyl methacrylate

To a stirred solution of thiophene-3-carboxaldehyde (1.00 g, 0.78 mL, 8.92 mmol) in anhydrous methanol (30 mL) at 0° C. was added sodium borohydride (0.35 g, 9.36 mmol) portion wise and stirring was continued for 2 h, during which time the mixture was allowed to warm to room temperature. The solution was concentrated and ethyl acetate (25 mL) and water (25 mL) were added. The layers were separated and the aqueous layer was extracted with ethyl acetate (2×25 mL). The combined organic layers were washed with water (2×25 mL), saturated brine (25 mL), dried (MgSO$_4$) and concentrated to afford thiophen-3-yl-methanol (1.01 g, 98%) as a brown oil. This material was used without further purification.

To a stirred solution of thiophen-3-ylmethanol (1.01 g, 8.92 mmol) and anhydrous pyridine (2.04 g, 2.08 mL, 25.82 mmol) in anhydrous dichloromethane (20 mL) at 0° C. was added methacryloylchloride (0.99 g, 0.92 mL, 9.81 mmol) dropwise and stirring was continued for 1 h, during which time the mixture was allowed to warm to room temperature. The solution was diluted with water (25 mL) and extracted with dichloromethane (3×25 mL). The combined organic layers were washed with 0.5 M hydrochloric acid (25 mL), water (2×25 mL), saturated brine (25 mL), dried (MgSO$_4$) and concentrated to give a brown oil. This material was purified using a Biotage Isolera automated chromatography system under normal phase conditions (silica column, gradient of 0→100% dichloromethane in petrol) with detection at 254 nm to afford thiophen-3-ylmethyl methacrylate (0.68 g, 44%) as a colorless oil. Rf 0.53 (petrol—dichloromethane, 2:3 v/v).

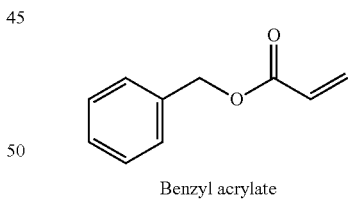

Benzyl acrylate

To a stirred solution of benzyl alcohol (2.00 g, 18.5 mmol) and triethylamine (4.67 g, 6.43 mL, 46.3 mmol) in anhydrous dichloromethane (25 mL) at room temperature was added acryloyl chloride (1.76 g, 1.58 mL, 19.4 mmol) dropwise and stirring was continued for 3 h. The solution was diluted with water (30 mL) and extracted with dichloromethane (2×30 mL). The combined organic layers were washed with saturated brine (30 mL), dried (MgSO$_4$) and concentrated to give an orange oil. The material was purified using a Biotage Isolera automated chromatography system under normal phase conditions (silica column, gradient of 7→60% ethyl acetate in petrol) with detection at 254 nm to afford benzyl acrylate (2.02 g, 67%) as a colorless oil. R$_f$ 0.69 (petrol—ethyl acetate, 7:3 v/v)

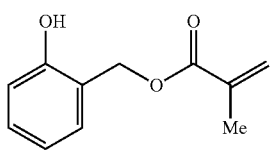

2-Hydroxybenzyl methacrylate

To a stirred solution of 2-hydroxylbenzyl alcohol (1.00 g, 8.06 mmol) and pyridine (1.91 g, 1.96 mL, 24.2 mmol) in anhydrous dichloromethane (10 mL) at 0° C. was added methacryloyl chloride (0.84 g, 0.78 mL, 8.06 mmol) dropwise and stirring was continued for 1 h whilst warming to room temperature. The solution was diluted with 0.5 M hydrochloric acid (10 mL), water (10 mL) and extracted with dichloromethane (3×10 mL). The combined organic layers were washed with saturated brine (25 mL), dried (MgSO$_4$) and concentrated to give a pale brown oil. The material was purified using a Biotage Isolera automated chromatography system under normal phase conditions (silica column, gradient of 15→100% dichloromethane in petrol) with detection at 254 nm to afford 2-hydroxybenzyl methacrylate (381 mg, 25%) as a colorless oil. R$_f$ 0.36 (dichloromethane—petrol 6:4 v/v)

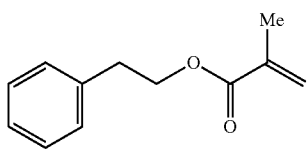

2-Phenylethylmethacrylate

To a stirred solution of 2-phenylethanol (2.50 g, 20.5 mmol) and triethylamine (6.20 g, 8.54 mL, 61.4 mmol) in anhydrous dichloromethane (35 mL) was added methacryloyl chloride (2.16 g, 2.00 mL, 20.7 mmol) dropwise and stirring was continued for 2 h at room temperature. The solution was diluted with water (30 mL) and extracted with dichloromethane (3×30 mL). The combined organic layers were washed with saturated brine (30 mL), dried (MgSO$_4$) and concentrated to give a yellow oil. The material was purified using a Biotage Isolera automated chromatography system under normal phase conditions (silica column, gradient of 7→42% ethyl acetate in petrol) with detection at 254 nm to afford 2-phenylethyl methacrylate (3.23 g, 83%) as a yellow oil.

R$_f$ 0.58 (petrol—ethyl acetate 7:3 v/v)

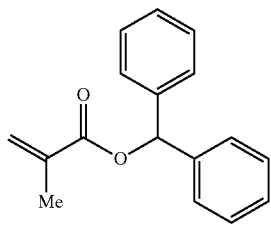

Benzhydryl methacrylate

To a stirred solution of benzhydrol (3.77 g, 20.5 mmol) and triethylamine (6.21 g, 8.55 mL, 61.4 mmol) in anhydrous dichloromethane (35 mL) was added methacryloyl chloride (2.16 g, 2.00 mL, 20.7 mmol) dropwise and stirring was continued for 2 h at room temperature. The solution was diluted with water (30 mL) and extracted with dichloromethane (2×20 mL). The combined organic layers were washed with saturated brine (40 mL), dried (MgSO$_4$) and concentrated to give an orange solid. The material was purified using a Biotage Isolera automated chromatography system under normal phase conditions (silica column, gradient of 7→33% ethyl acetate in petrol) with detection at 254 nm to afford benzhydryl methacrylate (3.85 g, 75%) as a white solid.

R$_f$ 0.77 (petrol—ethyl acetate 7:3 v/v)

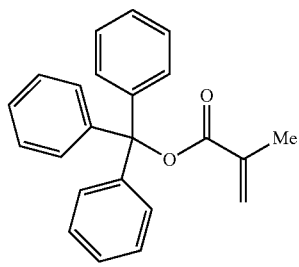

Triphenylmethylmethacrylate

To a stirred solution of triphenylmethyl chloride (6.11 g, 22.0 mmol) and triethylamine (11.1 g, 15.3 mL, 110 mmol) in anhydrous DME (60 mL) in an ice bath under N$_2$ was added methacrylic acid (9.47 g, 9.30 mL, 110 mmol) dropwise and stirring was continued for 1 h with warming to 80° C. The mixture was filtered through Celite and the filtrate washed with saturated aqueous NaHCO$_3$ (3×40 mL), saturated brine (30 mL), dried (MgSO$_4$) and concentrated to give a cream/white solid. The solid was dried in vacuo at room temperature for 3 h to give triphenylmethyl methacrylate as an off white solid (6.51 g, 90%). R$_f$ 0.52 (petrol—ethyl acetate 9:1 v/v)

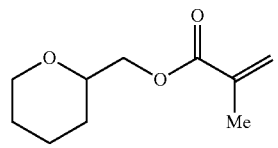

2-(Hydroxymethyl)tetrahydropyran methacrylate

To a stirred solution of 2-(hydroxymethyl) tetrahydropyran (2.75 g, 2.68 mL, 23.7 mmol) and triethylamine (7.18 g, 9.9 mL, 71.0 mmol) in anhydrous dichloromethane (40 mL) was added methacryloyl chloride (2.50 g, 2.31 mL, 23.9 mmol) dropwise and stirring was continued for 1 h. The solution was diluted with water (40 mL) and extracted with dichloromethane (3×10 mL). The combined organic layers were washed with saturated brine (30 mL), dried (MgSO$_4$) and concentrated to give an orange oil. The material was purified using a Biotage Isolera automated chromatography system under normal phase conditions (silica column, gradient of 7→54% ethyl acetate in petrol) with detection at 254 nm to afford 2-(hydroxymethyl) tetrahydropyran methacrylate (3.09 g, 71%) as a colorless oil. R$_f$ 0.66 (petrol—ethyl acetate 7:3 v/v)

Other Potential Monomers

Table 8 lists some other monomers that could be used in some embodiments of the present disclosure.

TABLE 8

Other Monomer Units

| Monomer | Monomer made in literature |
|---|---|
| Naphthalen-1-ylmethyl methacrylate | Yes |
| Tetrahydrofuran-2-ylmethyl methacrylate | Yes |
| Phenylethanol methacrylate | No |
| 3-Methoxybenzyl methacrylate | No |
| 1-Phenylethanol methacrylate | Yes |
| Thiophen-3-ylmethyl methacrylate | No |

Table 9 summarizes the biological properties of some of the tested monomers of the present disclosure.

TABLE 9

Summary of Biological Activity (silica, 15 μm, 300 Å particles)

| Compound | Biological Test |
|---|---|
| Styrene-divinylbenzene-methacrylate | Pass |
| Hydroxyvinylbenzene-divinylbenzene-methacrylate | Fail |
| Chlorovinylbenzene-divinylbenzene-allylalcohol | Fail |
| Styrene-2-hydroxyethylmethacrylate | Pass |
| 2(styrene)-2-hydroxyethylmethacrylate | Fail |
| Silica-styrene-2(2-hydroxyethylmethacrylate) | Fail |
| Styrene | Pass |
| Divinylbenzene | Fail |
| 2-hydroxyethylmethacrylate | Fail |
| Styrene-divinylbenzene-2-hydroxyethylmethacrylate | Fail |
| Benzylmethacrylate | Pass |
| Styrene-benzylmethacrylate | Pass |
| Styrene-divinylbenzene-benzylmethacrylate | Pass |
| Ethylmethacrylate | Pass |
| Styrene-ethylmethacrylate | Fail |
| Styrene-divinylbenzene-ethylmethacrylate | Fail |
| Cyclohexylmethacrylate | Fail |
| Furfurylmethacrylate | Fail |
| Napthalen-1-ylmethacrylate | Pass |
| Tetrahydrofuran-2-ylmethacrylate | Pass |
| Pyridin-3-ylmethacrylate | Fail |
| 3-methoxybenzylmethacrylate | Pass |
| 1-phenylethylmethacrylate | Pass |
| Thiophen-3ylmethylmethacrylate | Fail |
| Benzylacrylate | Pass |
| 2-hydroxybenzylmethacrylate | Pass |
| 2-phenylethylmethacrylate | Pass |
| Benzhydrylmethacrylate | Pass |
| 2-(hydroxymethyl)tetrahydropyran | Pass |

Monolithic Polymers

Sample Pre-Treatment

The following basic procedure was followed for all monolith sample preparations, excluding samples produced in plastic vessels for which glass pre-treatment could not be conducted. 0.1M sodium hydroxide wash (5 min), de-ionized water wash (20 min), methanol wash (5 min), dried under a stream of nitrogen, injected with 3-(trimethoxysilyl) propyl methacrylate (MSMA):methanol (1:1), seal vessel ends, vessel submerged in 35° C. water bath (17 h), methanol wash (13 min), de-ionized water wash (13 min), dried under a stream of nitrogen Monolith Polymerization Immediately after pre-conditioning the vessels could then be filled with the polymerization reaction mixture for functionalization, via radical polymerization. The reaction mixture composed of monomers, radical initiator and a porogenic solvent system, to be injected into the capillaries or other vessel, was prepared as such. The monomer mixture was premixed and included varied proportions of styrene (Sty), butylmethacrylate (But) and/or benzylmethacrylate (Bnz) with a crosslinking agent of divinylbenzene (DVB) or Ethylene glycol dimethacrylate (EDMA). Activating agents, vinylbenzenesulfonic acid (VBSA) and/or azobisisobutyronitrile (AIBN) were then added. One of two porogenic solvent systems was then added to the reaction mixture (cyclohexanol, water and NMP or 1-propan-1-ol, 1,4-butandiol). The monomer mixture was sonicated (15 min/until homogenization). The monolith vessels were then injected with monomer mixture and the ends were sealed. The remaining monomer mixture was transferred to a glass vial. The vessels were submerged in 70° C. water bath for 20 h or treated with UV light for 15 min. The samples were washed in methanol (15 min).

Figure 19:
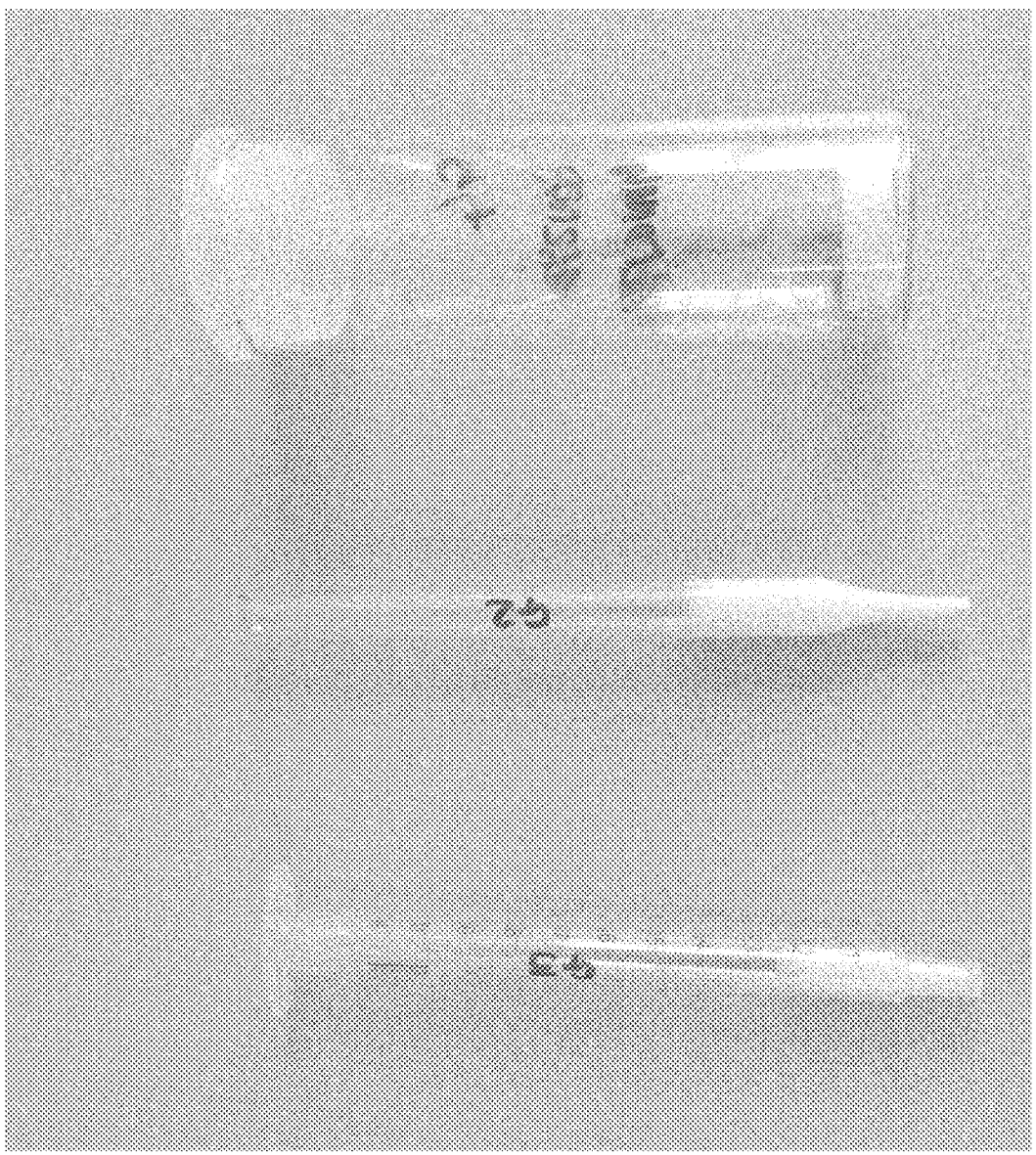
FIG. 19 shows monolith preparation within alternative packing formed in-situ, therefore structure and vessel independent.

A series of monolith preparations using a variety of monomer constitutions, with a range of porogenic solvent systems, in a variety of vessels have been prepared (Table 10 and FIG. 19). Vessels followed two formats: glass vials/plastic Eppendorf tubes for sample inspection and analysis; and forms designed for use in DNA extraction such as fused-silica glass capillaries, DNA extraction spin columns and other disposable filters and glass pipettes (Figure different packed columns).

TABLE 10

List of monolith prepared

| Format | Initiator Method | Monomer Composition | Porogenic System | Appearance and Integrity |
|---|---|---|---|---|
| Glass vials with pre-treatment | AIBN, VBSA heated at 70° C. | Bnz:Sty:DVB | Cyclohexanol:NMP:water | White solid, brittle |
| Glass vials without pre-treatment | AIBN, VBSA heated at 70° C. | Bnz:Sty:DVB | Cyclohexanol:NMP:water | White solid, very brittle |
| Polypropylene Eppendorf vials | AIBN, VBSA heated at 70° C. | Bnz:Sty:DVB | Cyclohexanol:NMP:water | White solid, Exceptionally brittle |
| Polypropylene Eppendorf vials | AIBN, VBSA heated at 70° C. | Bnz:DVB | Cyclohexanol:NMP:water | White solid, hard and waxy |

TABLE 10-continued

List of monolith prepared

| Format | Initiator Method | Monomer Composition | Porogenic System | Appearance and Integrity |
|---|---|---|---|---|
| Spin columns | AIBN, VBSA heated at 70° C. | Bnz:DVB | Cyclohexanol:NMP:water | White solid, brittle |
| Fused-silica capillary with pre-treatment | AIBN heated at 70° C. | Bnz:DVB | Cyclohexanol:NMP:water | White solid, brittle |
| Glass pipette with pre-treatment | AIBN heated at 70° C. | Bnz:DVB | Cyclohexanol:NMP:water | White solid, brittle |
| Plastic syringe | AIBN heated at 70° C. | Bnz:DVB | Cyclohexanol:NMP:water | White solid, brittle |
| Glass vials without pre-treatment | AIBN heated at 70° C. | Bnz:DVB | Cyclohexanol:NMP:water | White solid, brittle |
| Glass vials without pre-treatment | AIBN heated at 70° C. | Bnz:But:EDMA | 1-propanol:1,4-butandiol:water | White solid, brittle |
| Glass vial (as discs) without pre-treatment | AIBN heated at 70° C. | But:EDMA | 1-propanol:1,4-butandiol:water | White solid, brittle |
| Glass vial (as discs) without pre-treatment | AIBN heated at 70° C. | Bnz:EDMA | 1-propanol:1,4-butandiol:water | White solid, brittle |
| Fused-silica capillary with pre-treatment | AIBN heated at 70° C. | But:EDMA | 1-propanol:1,4-butandiol:water | White solid, brittle |
| Fused-silica capillary with pre-treatment | AIBN heated at 70° C. | Bnz:EDMA | 1-propanol:1,4-butandiol:water | White solid, brittle |
| Spin columns | AIBN heated at 70° C. | But:EDMA | 1-propanol:1,4-butandiol:water | White solid, brittle |
| Spin columns | AIBN heated at 70° C. | Bnz:EDMA | 1-propanol:1,4-butandiol:water | White solid, brittle |
| Spin columns | AIBN UV irradiation | Bnz:EDMA | 1-propanol:1,4-butandiol:water | White solid, brittle |
| Spin columns | AIBN Heated at 60° C. | Bnz:EDMA | 1-propanol:1,4-butandiol:water | White solid, brittle |

Functionalization of the inner surfaces of glass vials and fused-silica capillaries with alkenyl-bearing silanes allowed for monolith bonding directly to this substrate, this produced more robust and durable monoliths.

Figure 16A:
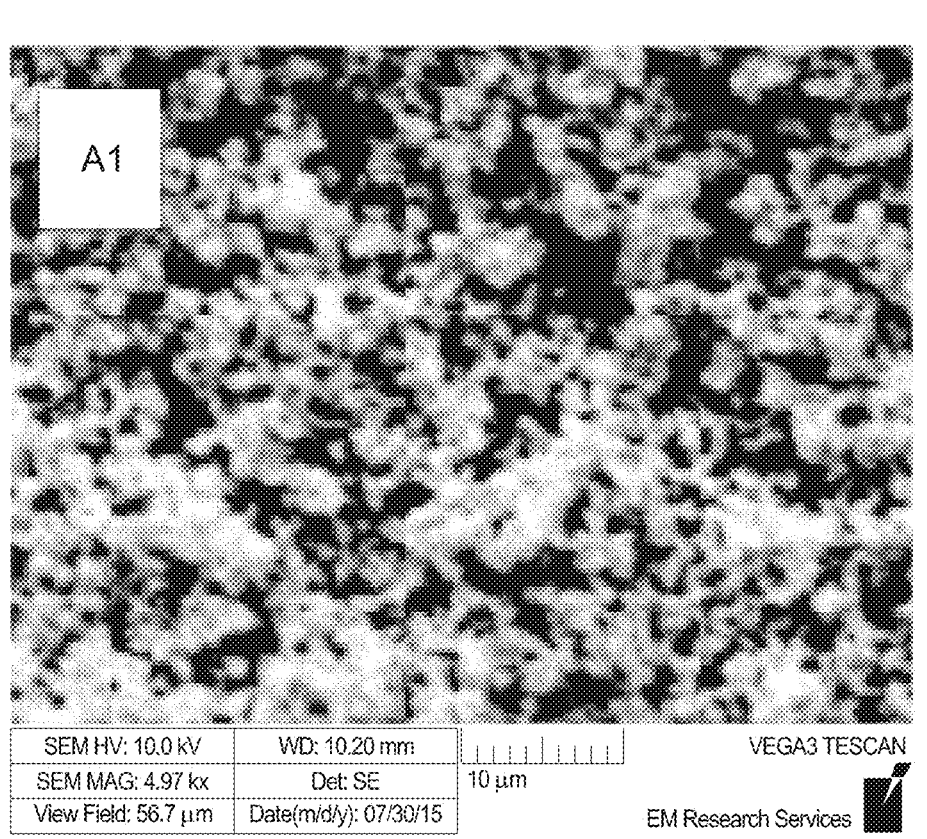
FIG. 16A shows SEM images of bulk monolith. The SEM magnification is 4.97 kx.
Figure 16B:
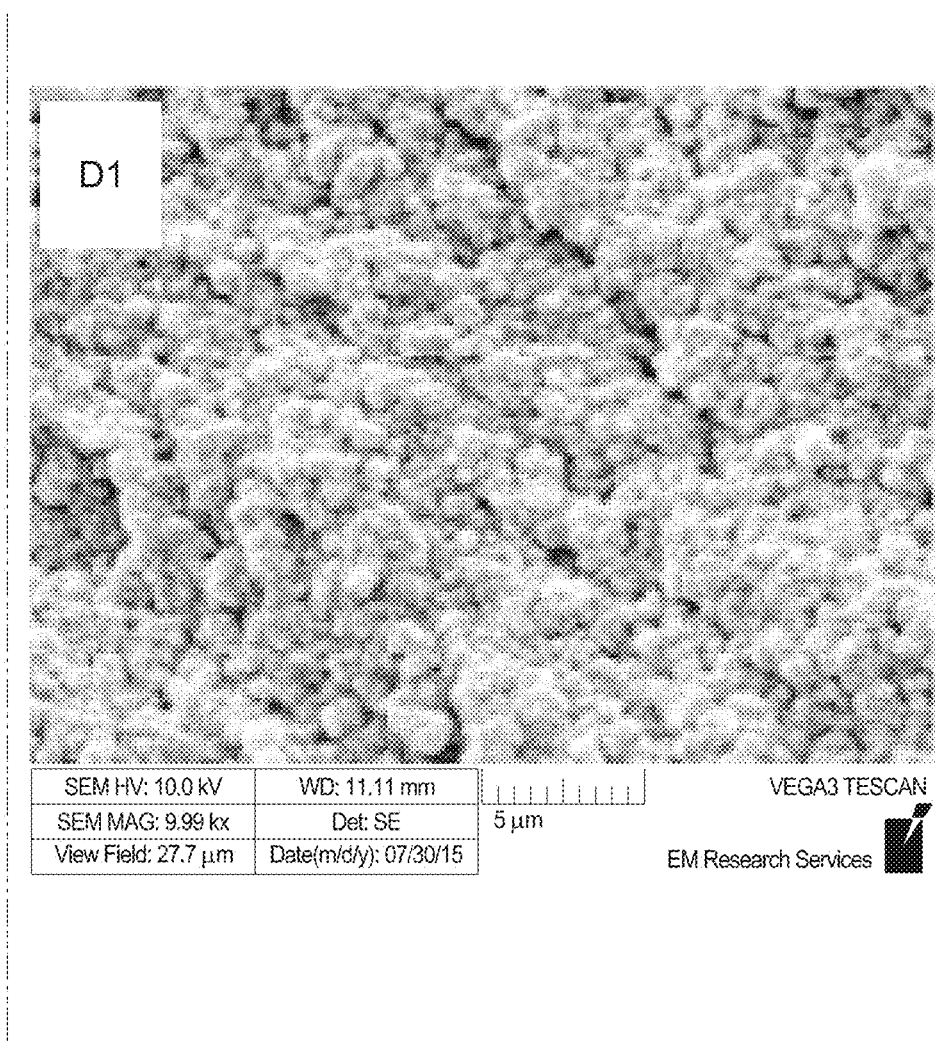
FIG. 16B shows SEM images of bulk monolith. The SEM magnification is 9.99 kx.

Monolith, composed of the benzyl methacrylate monomer, is shown to have a microporous structure (FIG. 16A-C, bulk monolith), lacking in macroporous character. A 50:50 mix of benzyl methacrylate and butyl methacrylate where by the addition of butyl methacrylate has significantly increased the porosity.

Figure 17A:
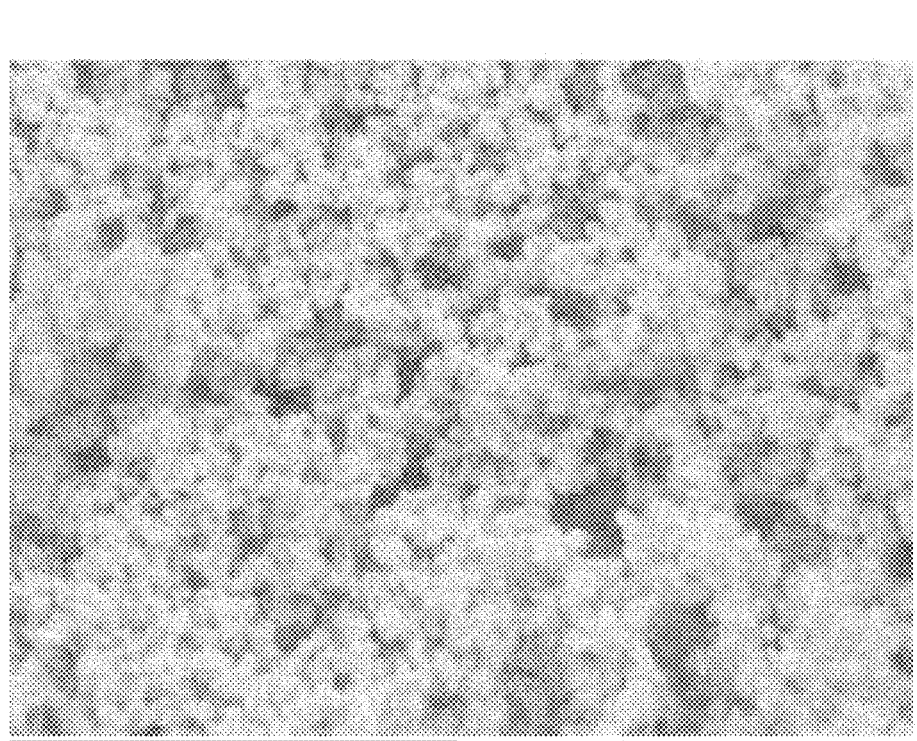
FIG. 17A shows SEM analysis results demonstrating a range of porous monoliths. Here, an SEM image of monolith composed on benzyl methacrylate monomer is shown.
Figure 17B:
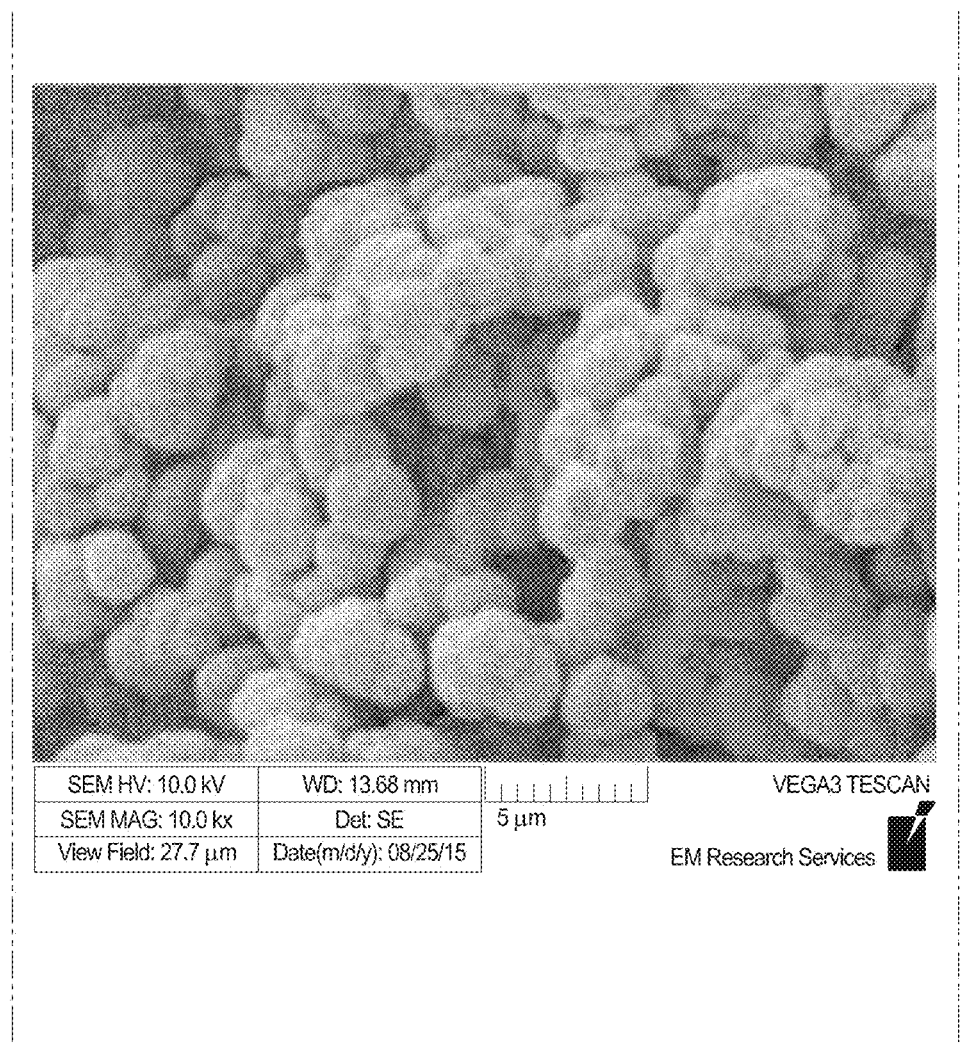
FIG. 17B shows an SEM image of 50:50 mixture of benzyl methacrylate and butyl methacrylate.

SEM analysis reveals successfully produce a range of porous monoliths. Monolith composed of the benzyl methacrylate monomer, is shown to have a microporous structure (FIG. 17A). A 50:50 mix of benzyl methacrylate and butyl methacrylate where by the addition of butyl methacrylate has significantly increased the porosity (FIG. 17B).

Figure 17C:
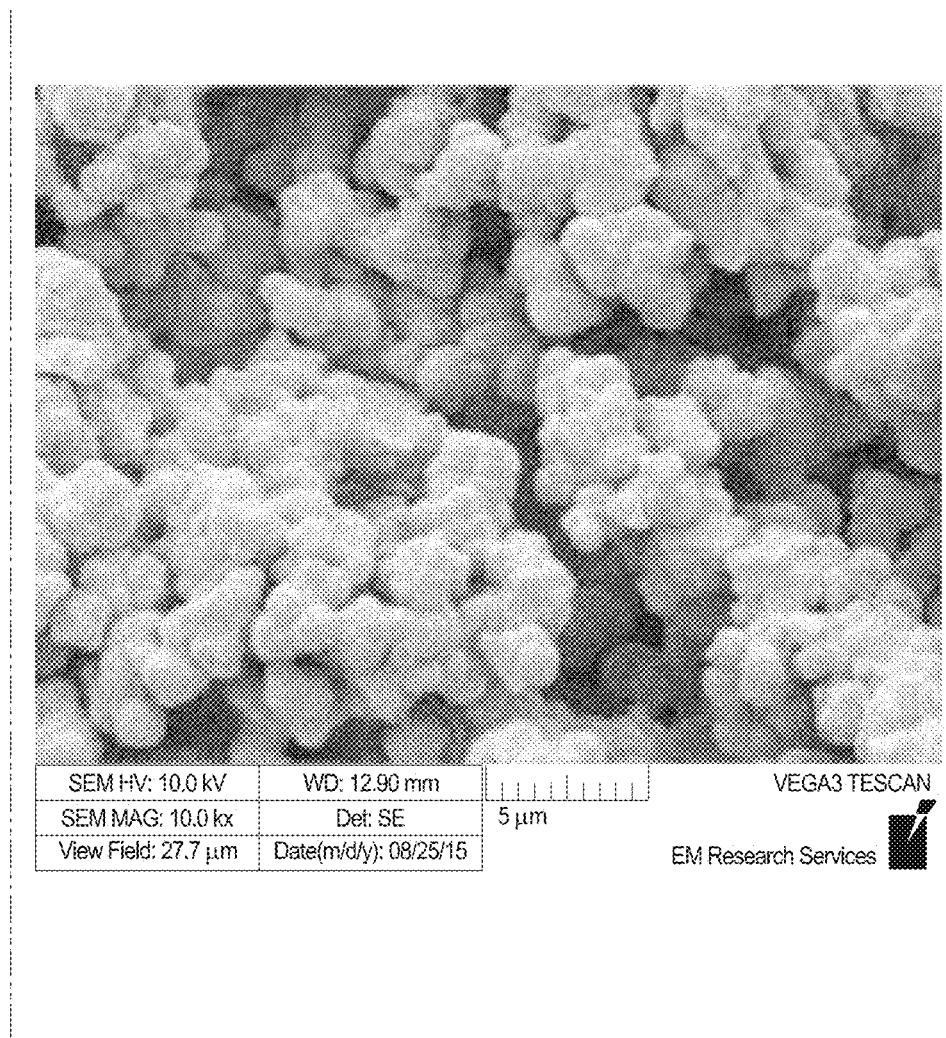
FIG. 17C shows an SEM image of monolith composed on butyl methacrylate.

Here Monolith displays both themacroporous and microporous feature, a quality for monolithic column flow through. Columns containing butyl methacrylate only which again exhibits both macroporous and microporous character (FIG. 17C). These findings highlight the role of incorporating an alkyl methacrylate component into the monomer reaction mixture to achieve the desired porosity characteristics. Similar to the silane modification of silica particles, the alkyl methacrylate component provides the appropriate surface wettability characteristics for adsorption of proteins and discrimination against whole scale DNA adhesion.

In-Field Application of Sorbent Material

Figure 18:
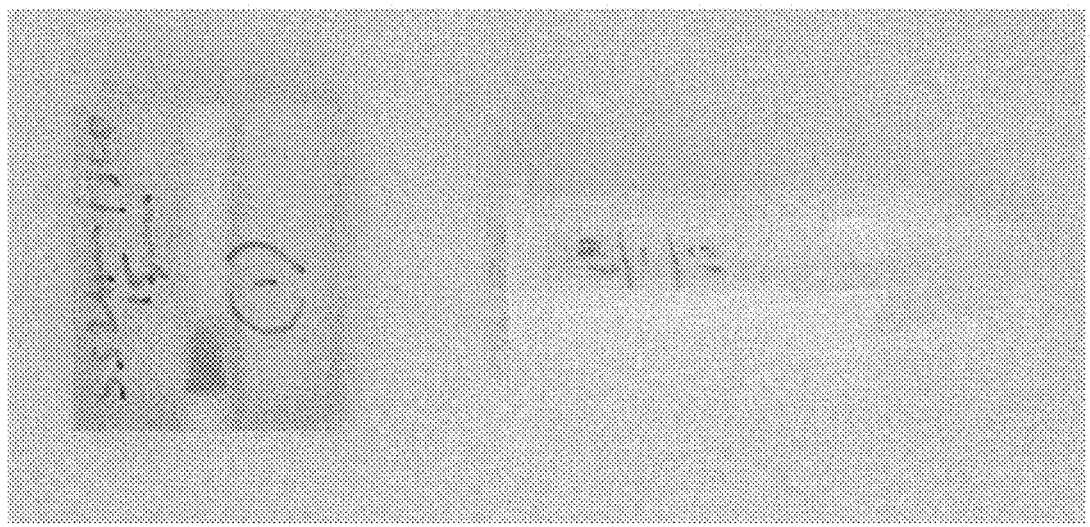
FIG. 18 shows a DNA extraction cassette (DEC) and a fraction produced by the DEC.
Figure 21:
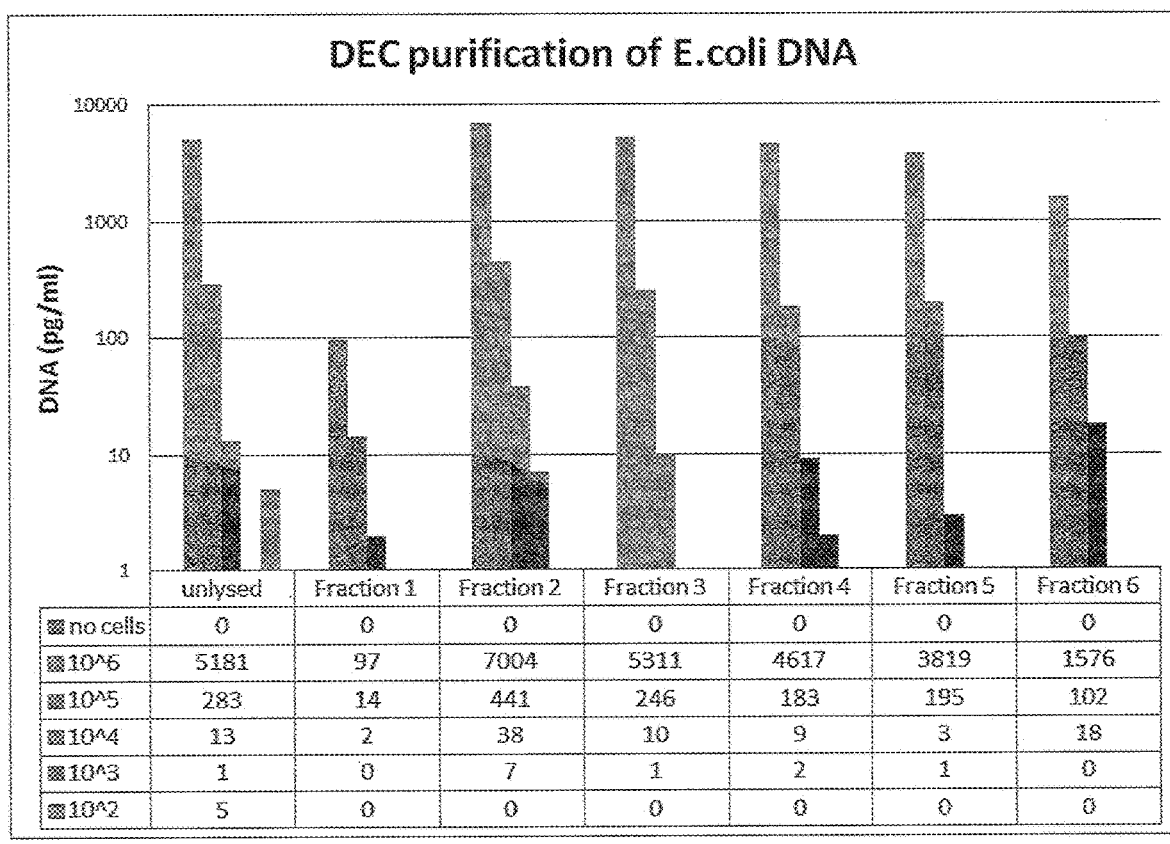
FIG. 21 shows E-coli extractions using continuous flow DECs.

In one example, DNA extraction cassettes (DECs, FIG. 18)—designed to hold sorbent material—have been used to purify DNA from 40 µl of blood lysate (generated by mechanical lysis using bead beating) or from Lysis Buffer alone. Previously described work has shown that DECs packed with sorbent (Tables 2-5) can purify DNA from blood lysate. FIG. 21 shows E-coli extractions using continuous flow DECs. The figure demonstrates the concentration of eluate DNA (pg/ml) in 100 ul fractions from DECs resulting from input lysis material derived from decreasing concentrations of E. coli samples (cells/ml).

Figure 20:
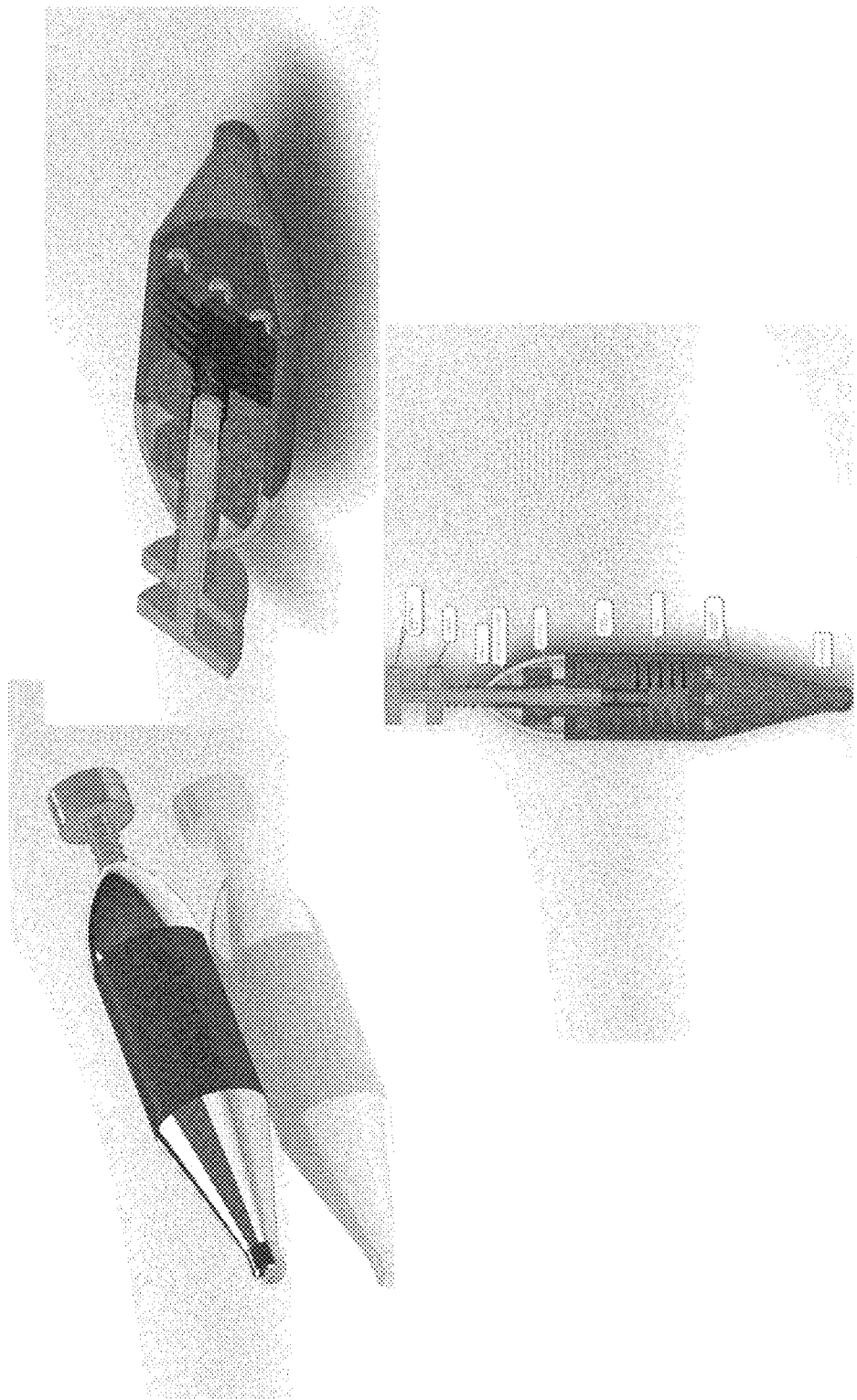
FIG. 20 shows an embodiment of a dual processing device that is capable of both lysing a biological sample and then passing the lysate through a sorbent filter.

In another example, this embodiment performs part of a dual processing device that is capable of both lysing a biological sample and then passing the lysate through the sorbent filter described. An exemplary embodiment of the device is illustrated in FIG. 20. Here, the cellular matrix binds to the sorbent material contained within the device whilst DNA is allowed to passes through the filter into a sample reception device that can be removed and stored/sent for analysis. The processing time is complete in under 5 minutes.

The device utilizes a sample reception port with a pressure sealed cap. The sample is placed into a lysis chamber that is controlled by a spring loaded plunger that allows the user to rotate a blade within the chamber and lyse the sample using either the blade itself or the beads within the chamber that are agitated. The sample chamber may also contain a buffer to act as mobility carrier through the extraction stage, or to aid lysis, either enzymatically or chemically, dependent on the need of the sample.

Simultaneously, the action of the mechanical lysis also builds pressure within the device. This build up in pressure provides the driving force to move the sample through the filter and allows the lysate to remain on the filter and the supernatant containing the DNA/RNA/Nucleic acids to flow into the sample reception "cap" that can then be removed and stored/analysed.

The release of the lysate to the extraction section of the device can be achieved by rotating the two sections to allow pressure release, or a separate piercing of a seal between to the two components.

In another example, spin columns are packed with silica beads coated with the polymers described. Typically, activation buffer is added and spun in the centrifuge for 1 minute. The spin speed is increased to 5000 rpm to elute the buffer. 80 µl of blood lysate was added to the columns in which the activation buffer had passed through; these were then spun at 5000 rpm for 1 minute. The eluents were collected and analyzed for their biological constituents by gel electrophoresis. With the format of a universal spin column and different protocols for each sample type DNA extraction has been performed on the following sample types.

Figure 22:
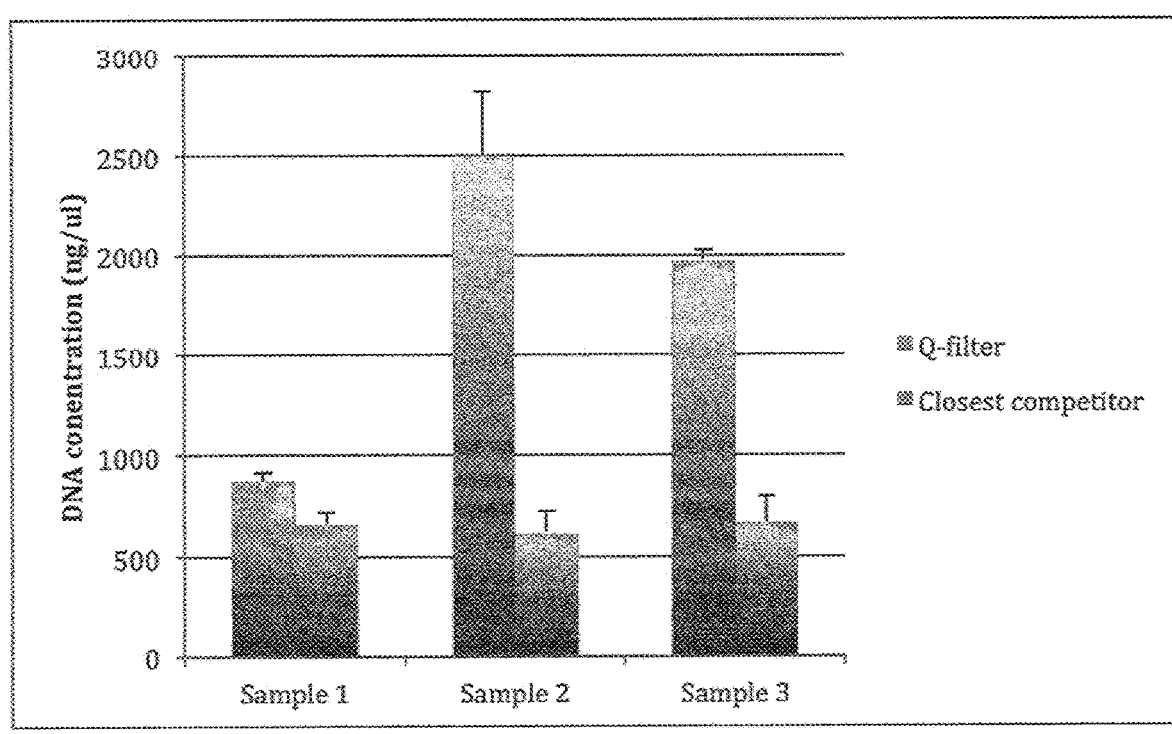
FIG. 22A shows the comparative data of DNA concentration between blood Q-filter and alternative devices (Blood Q-Filter vs Alternative Devices).
FIG. 22B shows data comparing DNA yield from Q-filter and alternative device (Blood Q-Filter vs Alternative Devices) for tissue (pinch biopsy).
FIG. 22C shows data comparing DNA yield from Q-filter and alternative device (Blood Q-Filter vs Alternative Devices) for bacterial plasmids.
FIG. 22D shows data comparing DNA yield from Q-filter and alternative device (Blood Q-Filter vs Alternative Devices) for buccal swabs.

Comparison of disclosed DNA extraction process (known form herein as 'Q-Filter') data for various sample types, using spin columns unless indicated. FIG. 22A shows the comparative data of DNA concentration between blood Q-filter and alternative devices (Blood Q-Filter vs Alternative Devices). FIGS. 22B-D show data comparing DNA yield from Q-filter and alternative device (Blood Q-Filter vs Alternative Devices) for tissue (pinch biopsy), bacterial plasmids and buccal swabs.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into sub ranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A sorbent material that will retain proteins and other non-nucleic acids but not nucleic acids, for separating bio-macromolecules, the sorbent material comprising a silanized material at least partially coated or formed with a polymer with a single repeating unit, wherein the polymer is selected from the group consisting of a poly(aryl methacrylate), a poly(aryl acrylate), a poly(heteroaryl methacrylate), and a poly(heteroaryl acrylate).

2. The sorbent material of claim 1, wherein the silanized material is a silanized inorganic material selected from the group consisting of a silanized silica particle, a silanized silica fiber and a silanized silica monolithic membrane or structure.

3. The sorbent material of claim 2, wherein the silanized inorganic material comprises silanized silica particles having an average pore size in the range of 1 nm to 100 nm.

4. The sorbent material of claim 3, wherein the average pore size is about 30 nm.

5. The sorbent material of claim 2, wherein the silanized inorganic material comprises silanized silica particles having an average diameter of less than about 200 microns.

6. The sorbent material of claim 5, wherein the average diameter is about 15 microns.

7. The sorbent material of claim 1, wherein the silanized material is an organic material selected from the group consisting of porous organic materials and membranes.

8. The sorbent material of claim 1, wherein the polymer comprises a recurring unit selected from the group consisting of benzyl methacrylate, anisolemethyl methacrylate, phenylethanol methacrylate, pyridinemethyl methacrylate and naphthalenemethyl methacrylate.

9. The sorbent material of claim 1, wherein the sorbent material has a wettability value in the range of 65° to 100°.

10. The sorbent material of claim 1, wherein the sorbent material has a surface area in the range of 0.1 $m^2$ to 130 $m^2$.

11. An article comprising the sorbent material of claim 1, wherein the article is in a particulate form, and wherein an average interstitial distance is greater than about 10 nm.

12. The article of claim 11, wherein the average interstitial distance is less than about 12 microns.

13. The article of claim 12, wherein the article is in the form of a membrane, and wherein the sorbent material is embedded in a porous organic or inorganic matrix.

14. A method of making a sorbent material that will retain proteins and other non-nucleic acids but not nucleic acids, comprising silanized silica at least partially coated with poly(benzyl methacrylate), the method comprising:
    suspending silica in a solution of dimethylvinylchlorosilane in trifluorotoluene;
    removing the liquid and resuspending the silica in a fresh solution of dimethylvinylchlorosilane in trifluorotoluene;
    optionally removing the liquid and resuspending the silica again in a fresh 5% solution of dimethylvinylchlorosilane in trifluorotoluene;
    collecting and drying the resulting silanized silica;
    adding the silanized silica, benzylmethacrylate and potassium peroxodisulfate to a stirred solution of sodium stearate in water; and
    collecting and drying the resultant sorbent material comprising silanized silica coated with poly(benzyl methacrylate).

* * * * *